(12) United States Patent
Kishore et al.

(10) Patent No.: US 11,354,990 B2
(45) Date of Patent: Jun. 7, 2022

(54) TREATMENT OF KIDNEY DISEASES ASSOCIATED WITH ELEVATED AVP

(71) Applicant: United States Government As Represented By The Department of Veterans Affairs, Washington, DC (US)

(72) Inventors: Bellamkonda K. Kishore, Sandy, UT (US); Yue Zhang, Salt Lake City, UT (US); Noel G. Carlson, Salt Lake City, UT (US)

(73) Assignee: THE UNITED STATES GOVERNMENT AS REPRESENTED BY THE DEPARTMENT OF VETERANS AFFAIRS

( * ) Notice: Subject to any disclaimer, the term of this patent is extended or adjusted under 35 U.S.C. 154(b) by 248 days.

(21) Appl. No.: 16/841,098

(22) Filed: Apr. 6, 2020

(65) Prior Publication Data
US 2020/0234552 A1 Jul. 23, 2020

Related U.S. Application Data

(62) Division of application No. 15/885,435, filed on Jan. 31, 2018, now Pat. No. 10,614,684.

(60) Provisional application No. 62/452,841, filed on Jan. 31, 2017.

(51) Int. Cl.
| | |
|---|---|
| A61K 31/7064 | (2006.01) |
| G08B 13/196 | (2006.01) |
| A61K 31/519 | (2006.01) |
| A61K 45/06 | (2006.01) |
| A61P 13/12 | (2006.01) |
| A61K 31/55 | (2006.01) |
| B64C 39/02 | (2006.01) |
| H04N 7/18 | (2006.01) |
| A61K 31/4365 | (2006.01) |
| A61K 38/095 | (2019.01) |

(52) U.S. Cl.
CPC .......... *G08B 13/196* (2013.01); *A61K 31/519* (2013.01); *A61K 31/55* (2013.01); *A61K 45/06* (2013.01); *A61P 13/12* (2018.01); *B64C 39/024* (2013.01); *H04N 7/185* (2013.01); *A61K 31/4365* (2013.01); *A61K 38/095* (2019.01); *B64C 2201/127* (2013.01)

(58) Field of Classification Search
CPC ........................ A61K 31/7064; C07D 2487/04
USPC ....................... 514/261.1; 544/254
See application file for complete search history.

(56) References Cited

U.S. PATENT DOCUMENTS

| | | | |
|---|---|---|---|
| 6,372,724 B1 | 4/2002 | Xu et al. | |
| 9,072,766 B2 | 7/2015 | Kahn et al. | |
| 2009/0297497 A1 | 12/2009 | Bellmkonda et al. | |
| 2015/0259692 A1 | 9/2015 | Bellmkonda et al. | |

FOREIGN PATENT DOCUMENTS

| | | |
|---|---|---|
| WO | WO-2005-100990 | 10/2005 |
| WO | WO-2006-052007 | 5/2006 |
| WO | WO-2006-060079 | 6/2006 |
| WO | WO-2014-066830 | 1/2014 |

OTHER PUBLICATIONS

U.S. Appl. No. 62/452,841, filed Jan. 31, 2017, Bellamkonda K. Kishore (The United States Government as Represented by the Department of Veterans Affairs).
U.S. Appl. No. 15/885,435 (U.S. Pat. No. 10,614,684), filed Jan. 31, 2018 (Apr. 7, 2020), Bellamkonda K. Kishore (The United States Government as Represented by the Department of Veterans Affairs).
Abe, M. (1955) A case of diabetes insipidus treated with germain (hayer 205),Tohoku Exp Med. 62(2): 128.
Agre, P. (2000) Homer W. Smith award lecture. Aquaporin water channels in kidney. J Am Soc Nephrol. 11(4): 764-77.
Ahmad, S, Storey RF. Development and clinical use of prasugrel and ticagrelor. Curr Pharm Des 18:5240-5260, 2012 PMID: 22724412.
Aihara, M, et al. Tolvaptan delays the onset of end-stage renal disease in a polycystic kidney disease model by suppressing increases in kidney volume and renal injury. J Pharmacol Exp Ther 349:258-267, 2014 PMID: 24570071.
Akoh, JA. Current management of autosomal dominant polycystic kidney disease. World JNephrol 4:468-479, 2015.
Alexander, SPH, et al. 2013. "The concise guide to pharmacology 2013/14: G protein-coupled receptors". British Journal of Pharmacology 170:1459-1581.

(Continued)

*Primary Examiner* — Jeffrey H Murray
(74) *Attorney, Agent, or Firm* — Ballard Spahr LLP

(57) ABSTRACT

Disclosed are methods for treating kidney disease including autosomal dominant polycystic kidney disease (ADPKD) in a subject, comprising the step of administering to the subject a composition comprising a therapeutically effective amount of ticagrelor or a derivative thereof, thereby treating ADPKD. Disclosed are methods of decreasing arginine vasopressin (AVP) production in a subject comprising the step of administering to the subject a composition comprising an effective amount of ticagrelor, thereby decreasing AVP production. Disclosed are methods for treating dilutional hyponatremia in a subject comprising the step of administering to the subject a composition comprising an effective amount of ticagrelor, thereby decreasing AVP production.

20 Claims, 9 Drawing Sheets

(56) References Cited

OTHER PUBLICATIONS

Bao, Y, et al. (2002) Prostaglandin transporter PGT is expressed in cell types that synthesize and release prostanoids. Am J Physiol Renal Physiol. 282(6): FI 103-10.

Baur, BP, and Meaney, CJ. Review of tolvaptan for autosomal dominant polycystic kidney disease. Pharmacother 34:605-616, 2014.

Belibi, FA, et al. Cyclic AMP promotes growth and secretion in human polycystic kidney epithelial cells. Kidney Int 66:964-973, 2004.

Bell, TN. (1994) Diabetes insipidus. Crit Care Nurs Clin North Arn.6(4): 675-85.

Bonventre, N. (1992) Phospholipase A2 and signal transduction. J Am Soc Nephrol. 3(2): 128-50.

Bonventre, N, and Nemenoff, R. (1991) Renal tubular arachidonic acid metabolism. Kidney Int. 39(3): 438-49.

Breyer, MD, and Breyer, RM. (2000) Prostaglandin E receptors and the kidney. J Am Physiol Renal Physiol. 279(1): F12-23.

Bonaca, MP, et al. Long-term use of ticagrelor in patients with prior myocardial infarction. New Eng J Med 372:1791-1800, 2015.

Chang, M-Y and Ong, ACM. New treatments for autosomal dominant polycystic kidney disease. Brit J Pharmacol 76:524-535, 2013.

Chen J, et al., 1997. Two new polymethoxylated flavones, a class of compounds with potential anticancer activity, isolated from cold pressed dancy tangerine peel oil solids. J Agric Food Chem 45:364-368.

Chebib. FC, et al. Vasopressin and disruption of calcium signaling in polycystic kidney disease. Nat Rev Nephrol 11;451-464, 2015.

Chou, CL, et al. (1998) Phosphoinositide signaling in rat inner medullary collecting duct. Am J Physiol. 274(3 Pt 2): F564-72.

Communi, D, et al. (2000) Advances in signalling by extracellular nucleotides. The role and transduction mechanisms of P2Y receptors. Cell Signal. 12(6): 351-60.

Digiovanni, SR, et al. (1994) Regulation of collecting duct water channel expression by vasopressin in Brattleboro rat. Proc NatlAcad Sci USA 91(19): 8984-88.

Di Renzo, GC, et al. (1981) Phosphatidylinositol-specific phospholipase C in fetal membranes and uterine decidua. J Clin Invest. 67(3): 847-56.

Ecelbarger, CA, et al. (1994) Extracellular ATP increases intracellular calcium in rat terminal collecting duct via a nucleotide receptor. Am J Physiol. 267(6 Pt 2): F998-1006.

Ecelbarger CA, et al. (1999) Decreased renal Na—K—2C1 cotransporter abundance in mice with heterozygous disruption of the G(s) alpha gene. Am J Physiol. 277(2 Pt 2): F235-44.

Ecelbarger CA, et al. (2001) Expression of salt and urea transporters in rat kidney during cisplatin-induced polyuria. Kidney Int. 60(6): 2274-82.

Endo, S, et al. (2002) Expression of PGT in MOCK cell monolayers: polarized apical localization and induction of active PG transport. Am J Physiol Renal Physiol. 282(4): F618-22.

Enjyoji K, et al. (1999) Targeted disruption of cd39/ATP diphosphohydrolase results in disordered hemostasis and thromboregulation. Nat Med. 5(9): 1010-17.

Erb, L, et al. Site-directed mutagenesis of P2U purinoceptors. Positively charged amino acids in transmembrane helices 6 and 7 affect agonist potency and specificity. (1995) J Biol Chem. 270(9): 4185-88.

Felix, R. A., et al. 2012. "Development of a comprehensive set of P2 receptor pharmacological research compounds". Purinergic Signaling S101-S112.

Fradet, Y, et al. (1980) Enhanced urinary prostaglandin E2 in postobstructive diuresis in humans. Prostaglandins Med. 5(1): 29-30.

Fradet, Y, et al. (1988) Renal prostaglandins in postobstructive diuresis. Comparative study of unilateral and bilateral obstruction in conscious dogs. Prostaglandins Leukot Essent Fatty Acids. 31(3): 123-29.

Frokiaer, J, et al. (1996) Bilateral ureteral obstruction downregulates expression of vasopressin-sensitive AQP-2 water channel in rat kidney. Am J Physiol. 270(4 Pt 2): F657-68.

Frokiaer, J, et al. (1998) Pathophysiology of aquaporin-2 in water balance disorders. Am J Med Sci. 316(5): 291-9.

Frokiaer, J, et al. (1999) Low aquaporin-2 levels in polyuric DI+/+ severe mice with constitutively high cAMP-phosphodiesterase activity. Am J Physiol. 276(2 Pt 2): FI 79-90.

Garcia-Villalba. P, et al. (2003) Real-time PCR quantification of AT1 and AT2 angiotensin receptor mRNA expression in the developing rat kidney. Nephron Exp Nephrol. 94(4): e154-59.

Gattone II GH, et al. Inhibition of renal cystic disease development and progression by vasopressin V2 receptors antagonists. Nature Med 9:1323-1326, 2003.

Geary, Antisense oligonucleotide pharmacokinetics and metabolism. Expert Opin. Drug Metab. Toxicol. (2009) 5(4): 381-391.

Gitlin, M. (1999) Lithium and the kidney: an updated review. Drug Saf. 20(3): 231-43.

Greenlee, W. J., American Chemical Society, Division of Medicinal Chemistry, Abstracts, 224th ACS National Meeting, Boston, MA, Aug. 18-22, 2002.

Han, JS, et al. (1994) Vasopressin-independent regulation of collecting duct water permeability. Am J Physiol. 266(1 Pt 2): F139-46.

Hannoaka, K, and Guggino, WB. cAMP regulates cell proliferation and cyst formation in autosomal polycystic kidney disease cells. J Am Soc Nephrol 11:1179-1187.

Homma S, et al. (1991) Role of cAMP-phosphodiesterase isozymes in pathogenesis ofmurine nephrogenic diabetes insipidus. Am J Physiol. 261(2 Pt 2): F345-53.

Hozawa, S, et al. (1996) cAMP motifs regulating transcription in the aquaporin 2 gene. Am J Physiol. 270(6 Pt 1): C1695-702.

Hsu, PD, et al. 2015, "Development and Applications of CRISPR-Cas9 for Genome Engineering." Cell 157(b): 1262-1278.

Hwang, EI, et al. (May 2003). "Production of plant-specific flavanones by *Escherichia coli* containing an artificial gene cluster". Appl. Environ. Microbiol. 69 (5): 2699-706.

Inscho, EW. (2001) Renal microvascular effects of P2 receptor stimulation. Clin Exp Pharmacol Physiol. 28(4): 332-39.

Ivanov, AI, et al. (2002) Prostaglandin E(2)-synthesizing enzymes in fever: differential transcriptional regulation. Am J Physiol Regul Integr Comp Physiol. 283(5): R1 104-17.

Jacobson, KA, et al. 2009. "Development of selective agonists and antagonists of P2Y receptors". Purinergic Signalling 5:75-89.

Jacobson, KA, et al. 2012. "Molecular structure of P2Y receptors: mutagenesis, modeling, and chemical probes". WIRES Membr Transp Signal 1:815-827.

Kaulich, M, et al. 2003. "Flavonoids—novel lead compounds for the development of P2Y2 receptor antagonists". Drug Development Research 59:72-81.

Kemp, PA et al. (2004) Am J Respir Cell Mol Biol 31: 446-455.

Kishore, BK, et al. Targeting renal purinergic signalling for the treatment of lithium-induced nephrogenic diabetes insipidus. Acta Physiol (Osf) 214:176-188, 2015.

Kishore, BK, et al. Extracellular nucleotide receptor inhibits AVP-stimulated water permeability in inner medullary collecting duct. Am J Physiol Renal Fluid Electro Physiol 269:F863-F869, 1995.

Kishore, BK, et al. P2Y2 receptors and water transport in the kidney (Review). Purinergic Signal 5:491-499, 2009.

Kishore, BK, et al. (2000) Cellular localization of P2Y(2) purinoceptor in rat renal inner medulla and lung. Am J Physiol Renal Physiol. 278(1): F43-51.

Kishore, BK, et al. (2000) Expression of renal aquaporins 1, 2, and 3 in a rat model of cisplatin-induced polyuria. Kidney Int. 58(2): 701-11.

Kishore, BK, et al. (2005) P2Y2 receptor mRNA and protein expression is altered in inner medullae of hydrated and dehydrated rats: Relevance to AVP-independent regulation of TMCD function. Am J Physiol Renal Physiol. 288: FI 164-F1172.

Kishore, BK, et al. (1996) Quantitation of aquaporin-2 abundance in microdissected collecting ducts: axial distribution and control by AVP. Am J Physiol. 271(1 Pt 2): F62-70.

Knepper MS, et al. Molecular physiology of water balance. New Eng J Med 1372:1349-1358, 2015.

(56) References Cited

OTHER PUBLICATIONS

Kohan, DE and Hughes, K. (1993) Autocrine role of endothelin in rat IMCD: Inhibition of AVP induced cAMP accumulation. Am J Physiol. Renal Physiol. 265:F126-F129, (1993).

Koyamada, N, et al. (1996) Apyrase administration prolongs discordant xenograft survival. Transplantation. 62(12): 1739-43.

Krane, CM, and Kishore, BK. (2003) Aquaporins: the membrane water channels of the biological world. Biologist. 50: 81-86.

Kwon, TH, et al. (2000) Altered expression of renal AQPs and Na(+) transporters in rats with lithium-induced NDI. Am J Physiol Renal Physiol. 279(3): F552-64.

Lantinga-Van Leeuwen, KS, et al. Kidney-specific inactivation of the Pkdl gene induces rapid cyst formation in developing kidneys and a slow onset of disease in adult mice. Human Mol Genet 16:3188-3196, 2007.

Laszlo, K, et al. (1980) Prostaglandin-dependent changes in renal haemodynamics and excretory patterns before and after release of 24 hours bilateral ureteral ligation. Acta Physiol Acad Sci Hung. 56(3): 309-23.

Laycock, JF, and Hanoune, J. (1998) From vasopressin receptor to water channel: intracellular traffic, constraint and by-pass. J Endocrinol. 159(3): 361-72.

Lenox, RH, et al. (1998) Neurobiology of lithium: an update. J Clin Psychiatry. 59 Suppl 6: 37-47.

Letsinger, RL, et al. (1989) Cholesteryl-conjugated oligonucleotides: synthesis, properties, and activity as inhibitors of replication of human immunodeficiency virus in cell culture. Proc Natl Acad Sci USA. 86(17): 6553-56.

Li, C, et al. (2004) Altered expression of urea transporters in response to ureteral obstruction. Am J Physiol Renal Physiol. 286(6): FI 154-62.

Li, C, et al. (2003) Altered expression of major renal Na transporters in rats with unilateral ureteral obstruction. Am J Physiol Renal Physiol. 284(1): F155-66.

Lin, LL, et al. (1993) cPLA2 is phosphorylated and activated by MAP kinase. Cell. 72(2): 269-78.

Lundquist, Islet Lysosomal enzyme activities and plasma insulin levels in obese hyperglycemic mice following the injection of the Lysosomotropic drug suramin, Diabetes Res. 2:207-211, 1985.

Mali, P, et al. 2013. "Cas9 as a versatile tool for engineering biology." Nature Methods 10:957-963.

Marples, D, et al. (1995) Lithium-induced downregulation of aquaporin-2 water channel expression in rat kidney medulla. J Clin Invest. 95(4): 1838-45.

Matsumura, Y, et al. (1997) Transcriptional regulation of aquaporin-2 water channel gene by cAMP. J Am Soc Nephrol. 8(6):861-67.

Mayer, R. 1999. Calycopterones and calyflorenones, novel biflavonoids from Calycopteris floribunda. J Nat Prod 62:1274-1278.

Mayer, R. 1990. Flavonoids from Leptospermum scoparium. Phytochemistry 29:1340-1342.

McHowat, J, and Creer, MH. (1998) Thrombin activates a membrane-associated calcium-independent PLA2 in ventricular myocytes. Am J Physiol. 274(2 Pt 1): C447-54.

Moses, AM, et al. (1986) Evidence for normal antidiuretic responses to endogenous and exogenous arginine vasopressin in patients with guanine nucleotide-binding stimulatory protein-deficient pseudohypoparathyroidism. J Clin Endocrinol Metab. 62(1): 221-24.

Murray, MD, and Brater, DC. (1993) Renal toxicity of the nonsteroidal anti-inflammatory drugs. Annu Rev Pharmacol Toxicol. 33: 435-65.

Murthy, KS, et al. (2002) PKA-dependent activation of PDE3A and PDE4 and inhibition of adenylyl cyclase VNI in smooth muscle. Am J Physiol Cell Physiol. 282(3): C508-17.

Nadler, SP, et al. (1992) PGE2 inhibits water permeability at a post-cAMP site in rat terminal inner medullary collecting duct. Am J Physiol. 262(2 Pt 2): F229-35.

Nielsen, S, et al. Vasopressin increases water permeability of kidney collecting duct by inducing translocation of aquaporin-CD water channels to plasma membrane. Proc Natl Acad Sci USA 92:103-1017, 1995.

Nielsen, S, et al. (1993) Cellular and subcellular immunolocalization of vasopressin-regulated water channel in rat kidney. Proc Natl Acad Sci USA. 90(24): 11663-67.

Nielsen, S, et al. (1999) Physiology and pathophysiology of renal aquaporins. J Am Soc Nephrol. 10(3): 647-63.

Nishizuka, Y. (1992) Intracellular signaling by hydrolysis of phospholipids and activation of protein kinase C. Science. 258(5082): 607-14.

Oksche, A, and Rosenthal, W. (1998) The molecular basis of nephrogenic diabetes insipidus. J Mol Med. 76(5): 326-37.

Ostrom, RS, et al. (2000) Stoichiometry and compartmentation in G protein-coupled receptor signaling: implications for therapeutic interventions involving G(s). J Pharmacol Exp Ther. 294(2): 407-12.

Phelan, KM, et al. (2003) Lithium interaction with the cyclooxygenase 2 inhibitors rofecoxib and celecoxib and other nonsteroidal anti-inflammatory drugs. J Clin Psychiatry. 64(11): 1328-34.

Piontek K, et al. A critical developmental switch defines the kinetics of kidney cyst formation after loss of Pkdl. Nature Med 12:1490-1495, 2007.

Ralevic, V, and Burnstock, G. 1998. Receptors for purines and pyrimidines. Pharmacol Rev 50:413-492.

Raphael, KL, et al. Inactivation of Pkdl in principal cells causes a more severe cystic kidney disease than in intercalated cells. Kidney Int 75:626-633, 2009.

Rice, WR, et al. (1995) Cloning and expression of the alveolar type II cell P2u-purinergic receptor. Am J Respir Cell Mol Biol. 12(1): 27-32.

Rieg, et al., Mice lacking P2Y2 receptors have salt-resistant hypertension and facilitated renal Na+ and water reabsorbtion 2007, FASEB J 21:3717-3726.

Rinschen, MM, et al. Vasopressin-2 receptor signaling and autosomal dominant polycystic kidney disease: from bench to bedside and back again. J Am Soc Nephrol 25:1140-1147, 2014.

Roman, RJ, and Lechene, C. (1981) Prostaglandin E2 and F2 alpha reduces urea reabsorption from the rat collecting duct. Am J Physiol. 241(1): F53-60.

Rouch, AJ, and Kudo, LH. (2000) Role of PGE(2) in alpha(2)-induced inhibition of AVP- and CAMP-stimulated H(2)0, Na(+), and urea transport in rat IMCD. Am J Physiol Renal Physiol. 279(2): F294-301.

Rouse, D, et al. (1994) ATP inhibits the hydrosmotic effect of AVP in rabbit CCT: evidence for a nucleotide P2u receptor. Am J Physiol. 267(2 Pt 2): F289-95.

Sakairi, T, et al. Nestin expression in the kidney with an obstructed ureter. Kidney Int 72:307-318, 2007.

Schwiebert, EM, et al. (2001) Extracellular nucleotide signaling along the renal epithelium. Am J Physiol Renal Physiol. 280(6): F945-63.

Sheikh-Hamad, D, et al. (2004) Cellular and molecular studies on cisplatin-induced apoptotic cell death in rat kidney. Arch Toxicol. 78(3): 147-55.

Shillingford, JM, et al. Rapamycin ameliorates PKD resulting from conditional inactivation of Pkdl. J Am Soc Nephrol 21:489-497, 2010.

Shoji, Y, et al. (2004) Downregulation of prostaglandin E receptor subtype EP3 during colon cancer development. Gut. 53(8): 1151-58.

Sonnenberg, H, and Wilson, DR. (1976) The role of the medullary collecting ducts in postobstructive diuresis. J Clin Invest. 57(6): 1564-74.

Sugawara, M, et al. (1988) Involvement of prostaglandin E2, cAMP, and vasopressin in lithium-induced polyuria. Am J Physiol. 254(6 Pt 2): R863-69.

Sun, R, et al. (2005) Chronic dDAVP infusion in rats decreases the expression of P2Y2 receptor in inner medulla and P2Y2 receptor-mediated PGE2 release by IMCD. Am J Physiol Renal Physiol. 289(4): F768-76.

Sun, R, et al. (2005) P2Y2 receptor-mediated release of prostaglandin E2 by IMCD is altered in hydrated and dehydrated rats: relevance to AVP-independent regulation of IMCD function. Am J Physiol Renal Physiol. 289(3): F585-92.

Takakura A, et al. Pkd1 inactivation induced in adulthood produces focal cystic disease. J Am Soc Nephrol 19:2351-2363, 2008.

(56) References Cited

OTHER PUBLICATIONS

Takeda, S, et al. (1991) High activity oflow-Michaelis-Menten constant 3', 5'-cyclic adenosine monophosphate-phosphodiesterase isozymes in renal inner medulla of mice with hereditary nephrogenic diabetes insipidus. Endocrinology. 129(1): 287-94.
Teitelbaum, I. (1992) Hormone signaling systems in inner medullary collecting ducts. Am J Physiol. 263(6 Pt 2): F985-90.
Terris, J, et al. (1998) Long-term regulation of renal urea transporter protein expression in rat. J Am Soc Nephrol. 9(5): 729-36.
Timmer, RT, and Sands, JM. (1999) Lithium intoxication. J Am Soc Nephrol. 10(3): 666-74.
Tomioka M, et al. Nestin is a novel marker for renal tubulointerstitial injury in immunoglobulin A nephropathy. Nephrology 15:568-574, (2010); 15(5); 568-574.
Torres, VE. Role of vasopressin antagonists. Clin JAm Soc Nephrol 3:1212-1218, 2008.
Torres, VE. Vasopressin antagonists in polycystic kidney disease. Semin Nephrol 28:306-317, 2008.
Torres, VE, and Harris, PC. Autosomal dominant polycystic kidney disease: the last 3 years. Kidney Int 76:149-168, 2009.
Torres, VE, and Harris, PC. Strategies targeting cAMP signalling in the treatment of polycystic kidney disease. J Am Soc Nephrol 25:18-32, 2014.
Torres, VE, et al. Rationale an design of the TEMPO 3-4 study, tolvaptan efficacy and safety in management of autosomal dominant polycystic kidney disease and its outcomes. Am J Kidney Dis 57:692-699, 2011.
Trantas, E, et al. (2009). "Metabolic engineering of the complete pathway leading to heterologous biosynthesis of various flavonoids and stilbenoids in *Saccharomyces cerevisiae*". Metabolic Engineering 11 (6): 355-366.
Vallon, V. (2008) P2 receptors in the regulation of renal transport mechanisms. Am J Physiol Renal Physiol., 294(1): F10-27.
Van Rhee, AM, et al. (1995) Modelling the P2Y purinoceptor using rhodopsin as template. Drug Des Discov. 13(2): 133-54.
Ververidis, F, et al. (Oct. 2007). "Biotechnology of flavonoids and other phenylpropanoid-derived natural products. Part I: Chemical diversity, impacts on plant biology and human health". Biotechnology Journal 2 (10): 1214-34.
Ververidis, F, et al. (2007). "Biotechnology of flavonoids and other phenylpropanoid-derived natural products. Part II: Reconstruction of multienzyme pathways in plants and microbes". Biotechnology Journal 2 (10): 1235-49.
Wallentin, L. P2Y12 inhibitors: Differences in properties and mechanisms of action and potential consequences for clinical use. Eur Heart J30:1964-1977, 2009.
Wang, X, et al. Effectiveness of vasopressin V2 receptor antagonists OPD-31260 on polycystic kidney disease development in the PKC rat. J Am Soc Nephrol 16:846-851, 2005.
Wang, W, et al. (2002) AQP3, p-AQP2, and AQP2 expression is reduced in polyuric rats with hypercalcemia: prevention by cAMP-PDE inhibitors. Am J Physiol Renal Phvsiol. 283(6): F1313-25.
Wang, X, et al. Vasopressin directly regulates cyst growth in polycystic kidney disease. JAm Soc Nephrol 19:102-108, 2008.
Welch, BD, et al. (2003) P2Y2 receptor-stimulated release of prostaglandin E2 by rat inner medullary collecting duct preparations. Am J Physiol Renal Physiol. 285(4): F711-21.
Williams, M. (2000) Purines: from premise to promise. J Auton Nery Syst. 81(1-3): 285-28.
Yang, T, et al. (1999) Regulation of cyclooxygenase-2 expression in renal medulla by tonicity in vivo and in vitro. Am J Physiol. 277(1 Pt 2): FI-9.
Yasui, M, et al. (1997) Adenylate cyclase-coupled vasopressin receptor activates AQP2 promoter via a dual effect on CRE and AP1 elements. Am J Physiol. 272(4 Pt 2): F443-50.
Zelenina, M, et al. (2000) Prostaglandin E(2) interaction with AVP: effects on AQP2 phosphorylation and distribution. Am J Physiol Renal Physiol. 278(3): F388-94.
Zhang, Y, et al. Clopidogrel attenuates lithium-induced alterations in renal water and sodium channels/transporters in mice. Purinergic Signal 11:507-518, 2015.
Zhang, Y, et al. P2Y12 receptor localizes in the renal collecting duct and its blockade augments arginine vasopressin action and alleviates nephrogenic diabetes insipidus. J Am Soc Nephrol 26:2979-2987, 2015.
Zhang, Y, et al., Genetic deletion of the P2Y2 receptor offers significant resistance to development of lithium-induced polyuria accompanied by alterations in PGE2 signaling, Am J Physiol Renal Physiol 302: F70-F77, 2012.
Zhang, Y, et al., Attenuation of lithium-induced natriuresis and kaliuresis in P2Y2 receptor knockout mice, Am JPhysiol Renal Physiol 305: F407-F416, 2013.
Zhang, Y, et al., Prasugrel suppresses development of lithium-induced nephrogenic diabetes insipidus in mice, Purinergic Signal Jun. 2017; 13(2): 239-248.

| Comparison | P value |
|---|---|
| Controls (CNT) vs. dDAVP | NS |
| dDAVP vs. dDAVP+Ticagrelor 2 µM | <0.05 |
| dDAVP vs. dDAVP+Ticagrelor 10 µM | <0.001 |
| dDAVP+Tica 0.5 µM vs. dDAVP+Tica 10 µM | <0.05 |

| Comparison | P value |
|---|---|
| CNT vs. dDAVP | <0.001 |
| CNT Vs. dDAVP+Tica 0.5 | <0.001 |
| dDAVP vs. dDAVP+Tica 2 μM | <0.01 |
| dDAVP vs. dDAVP+Tica 10 μM | <0.001 |
| dDAVP+Tica 0.5 μM vs. dDAVP+Tica 2 μM | N.S. |
| dDAVP+Tica 0.5 μM vs. dDAVP+Tica 10 μM | <0.001 |
| dDAVP+Tica 2 μM vs. dDAVP+Tica 10 μM | <0.01 |

TREATMENT OF KIDNEY DISEASES ASSOCIATED WITH ELEVATED AVP

STATEMENT REGARDING FEDERALLY SPONSORED RESEARCH

This invention was made with government support under IOBX000596 awarded by the U.S. Department of Veterans Affairs. The government has certain rights in the invention.

CROSS-REFERENCE TO RELATED PATENT APPLICATIONS

This patent application is a divisional application of U.S. patent application Ser. No. 15/885,435, filed Jan. 31, 2018 (U.S. Pat. No. 10,614,684), which claims the benefit of the filing date of U.S. Ser. No. 62/452,841, filed Jan. 31, 2017. The content of these earlier filed applications is hereby incorporated by reference in their entirety into the present patent application.

BACKGROUND OF THE INVENTION

Ticagrelor (Brilinta®) has been in clinical use as an anti-clotting drug, but not for the treatment of cystic disease. Autosomal dominant polycystic kidney disease (ADPKD) is the most common inherited disease of the kidney, with a prevalence at birth ranging from 1 per 500 to 1000 people worldwide. ADPKD is caused by mutations in the PKD1 (85%) or PKD2 (15%) genes, which encode for polycystin-1 or polycystin-2 proteins, respectively. The hallmark of ADPKD is the formation of cysts in both kidneys, which gradually grow in size. Over the decades, new cysts form resulting in a decline of kidney function. By the age 55 years, about 50% of the ADPKD patients develop end-stage renal disease (ESRD), which requires dialysis therapy or renal transplantation.

There is no specific therapy for ADPKD. Its management is limited to control of high blood pressure, and symptomatic treatment of complications. Currently three different approaches are being tested to slow down the progression of cyst growth, but each has its own significant side effects.

Therefore, finding a treatment that can be sustained long-term without significant side effects is needed. The disclosed methods provide a new treatment for kidney diseases associated with elevated AVP (such as ADPKD) with a drug that is known to be safe for long term use in patients.

SUMMARY OF THE INVENTION

Disclosed are methods for treating kidney diseases associated with elevated AVP (such as ADPKD) in a subject, comprising the step of administering to the subject a composition comprising a therapeutically effective amount of ticagrelor or a derivative thereof, thereby treating the kidney disease in the subject.

Disclosed are methods for treating autosomal dominant polycystic kidney disease (ADPKD) in a subject, comprising the step of administering to the subject a composition comprising a therapeutically effective amount of ticagrelor or a derivative thereof, thereby treating ADPKD, wherein treating ADPKD comprises reducing cyst number and/or size or decreasing or preventing the increase in kidney size.

Disclosed are methods for treating ADPKD in a subject, comprising the step of administering to the subject a composition comprising a therapeutically effective amount of ticagrelor or a derivative thereof, thereby treating ADPKD, further comprising administering one or more additional therapeutics.

Disclosed are methods for treating a disease (such as ADPKD) associated with elevated AVP in a subject suffering therefrom, comprising the step of administering to the subject a composition comprising a therapeutically effective amount of ticagrelor or a derivative thereof, thereby treating the disease in the subject.

Disclosed are methods of decreasing arginine vasopressin (AVP) production in a subject comprising the step of administering to the subject a composition comprising an effective amount of ticagrelor, thereby decreasing AVP production.

Disclosed are methods for treating dilutional hyponatremia in a subject comprising the step of administering to the subject a composition comprising an effective amount of ticagrelor, thereby decreasing AVP production.

Disclosed are methods for treating ADPKD in a subject suffering therefrom, comprising the step of administering to the subject a composition comprising a therapeutically effective amount of ticagrelor or a derivative thereof, thereby treating ADPKD in the subject.

Disclosed are methods for inhibiting arginine vasopressin (AVP) production in hypothalamus comprising administering to hypothalamic cells or contacting hypothalamic cells with an effective amount of ticagrelor or a derivative thereof, thereby inhibiting arginine vasopressin (AVP) production in hypothalamic cells.

Disclosed are methods for inhibiting arginine vasopressin (AVP) production in a subject in need thereof, comprising administering to the subject a composition comprising an effective amount of ticagrelor or a derivative thereof, thereby decreasing AVP production in the subject.

Disclosed are methods for inhibiting cyst growth in a kidney of a subject suffering from a kidney disease (such as ADPKD) associated with elevated AVP, comprising administering to the subject a composition comprising an effective amount of ticagrelor or a derivative thereof, thereby inhibiting cyst growth in a kidney of the subject.

Disclosed are methods for lowering circulating levels of AVP in a subject, comprising administering to the subject an effective amount of a composition comprising an effective amount of ticagrelor or a derivative thereof, thereby lowering circulating levels of AVP in the subject.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
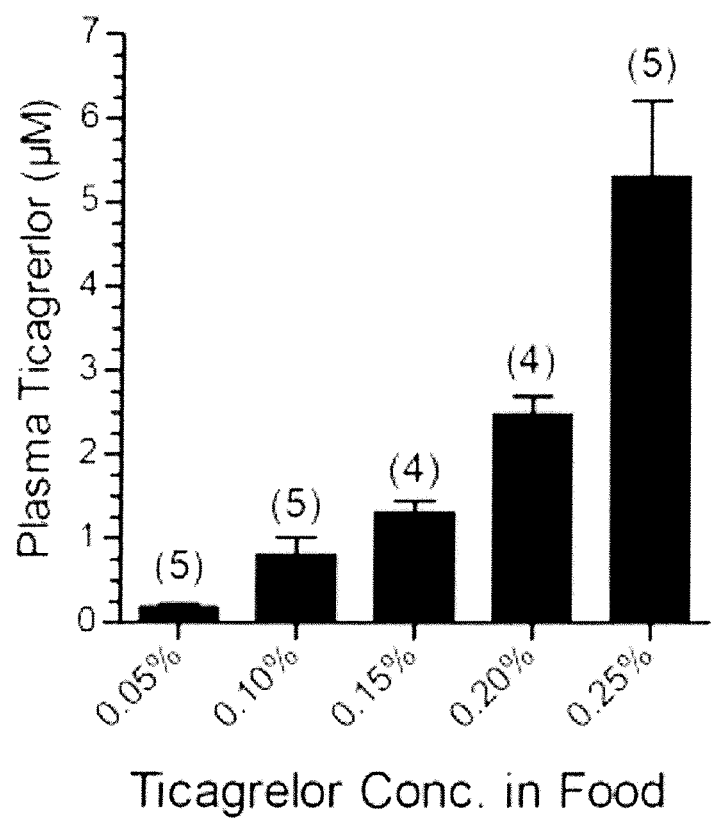
FIG. 1 is a graph showing the effect of feeding different concentrations of ticagrelor in the diet on plasma ticagrelor levels. (Numbers in parentheses are number of mice in each group).
Figure 2:
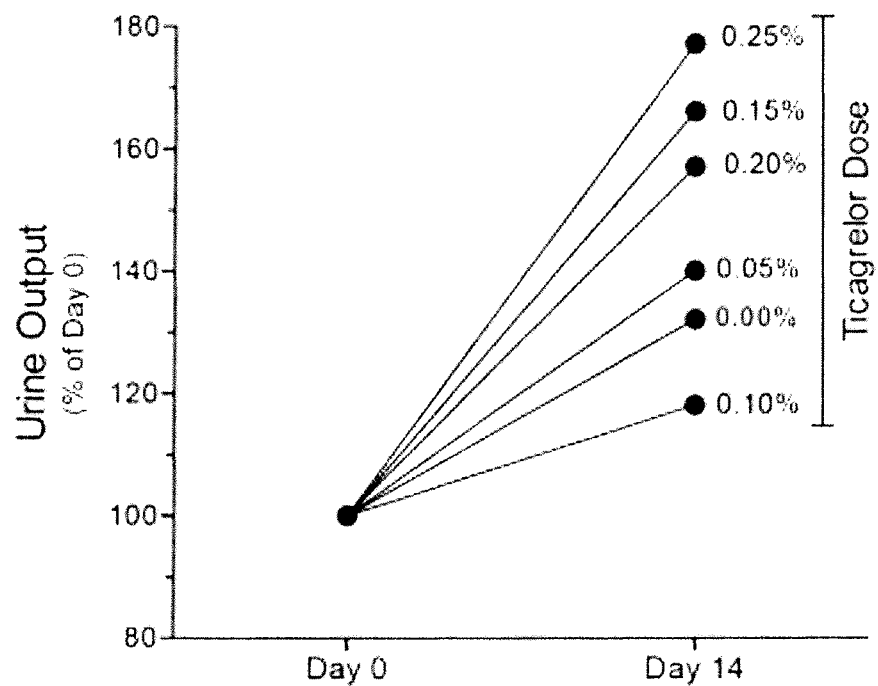
FIG. 2 is a graph showing the changes in the mean urine outputs in mice fed different concentrations of ticagrelor as a function of time. The lines show the percent increase in urine outputs from day 0 to day 14.
Figure 3:
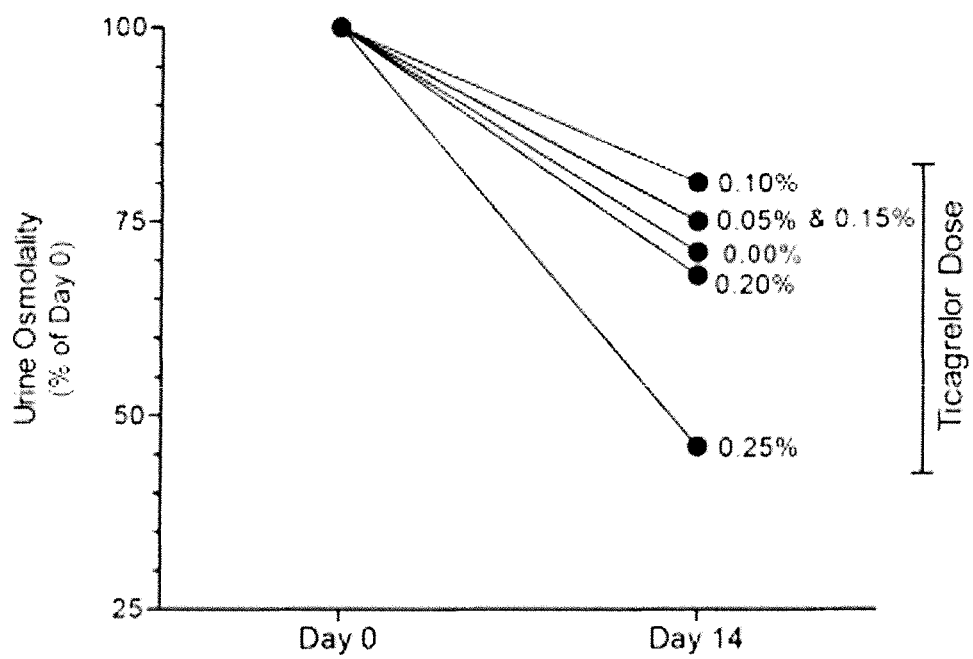
FIG. 3 is a graph showing the changes in the mean urine osmolalities in mice fed different concentrations of ticagrelor as a function of time. The lines show the percent fall in urine osmolalities from day 0 to day 14.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a derivative of ticagrelor is disclosed and discussed and a number of modifications that can be made to a number of molecules are discussed, each and every combination and permutation of derivative and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D.

Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Other than in the operating examples, or where otherwise indicated, all numbers expressing quantities of ingredients or reaction conditions used herein should be understood as modified in all instances by the term "about." The term "about" when used in connection with percentages can mean a range of ±1-10%.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Thus, for example, reference to "a therapeutic" includes a plurality of such therapeutics; reference to "the therapeutic" is a reference to one or more therapeutics known to those skilled in the art, and so forth.

The use of the term "containing," as well as other forms, such as "contains" and "contained," is not limiting. Also, terms such as "element" or "component" encompass both elements or components comprising one unit and elements or components comprising more than one unit unless specifically stated otherwise.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

The term "therapeutic" refers to a composition that treats a disease. For example, the therapeutics disclosed herein are compositions that treat autosomal dominant polycystic kidney disease.

As used herein, the term "subject" or "patient" refers to any organism to which a composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like.

As used herein, the term "therapeutically effective amount" means an amount of a therapeutic, prophylactic, and/or diagnostic agent (e.g., ticagrelor) that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition. In some instances, a therapeutically effective amount is an amount of a therapeutic that provides a therapeutic benefit to an individual.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. For example, "treating" a kidney disease, e.g., autosomal dominant polycystic kidney disease, may refer to slowing down the progression of the disease, reducing the number or size of cysts, and/or reducing the size of the kidneys. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the term "derivative" refers to a compound having a structure derived from the structure of a parent compound (e.g., ticagrelor) and whose structure is sufficiently similar to those disclosed herein and based upon that similarity, would be expected by one skilled in the art to exhibit the same or similar activities and utilities as ticagrelor, or to induce, as a precursor, the same or similar activities and utilities as ticagrelor. Exemplary derivatives include salts, esters, amides, salts of esters or amides, and N-oxides of a parent compound.

As used herein, the term "production of arginine vasopressin or AVP" refers to or encompasses transcription of AVP gene or processing of the mRNA or translation or post-translational modification or storage or secretion of a combination of one of more of these.

Ranges may be expressed herein as from "about" one particular value, and/or to "about" another particular value. When such a range is expressed, also specifically contemplated and considered disclosed is the range¬from the one particular value and/or to the other particular value unless the context specifically indicates otherwise.

Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Methods for Treating Kidney Diseases

Disclosed are methods for treating kidney diseases including those associated with elevated AVP (such as ADPKD) in a subject, comprising the step of administering to the subject a composition comprising a therapeutically effective amount of ticagrelor or a derivative thereof, thereby treating the kidney disease in the subject. In an embodiment, ADPKD is associated with mutation of PKD1 gene and/or PKD2 gene. In another embodiment, ADPKD is associated with altered expression of PKD1 gene and/or PKD2 gene. In another embodiment, ADPKD is associated with reduced expression of PKD1 gene and/or PKD2 gene.

As used herein, "elevated" (such as elevated AVP) means a level higher than found in normal patients (patients without a kidney disease). In the case of elevated AVP, in one embodiment, the determination of an elevated AVP may be based on comparison of measured plasma AVP level of a subject to the mean plasma AVP level and its standard deviation for a reference normal population. See for example, van Londen, L. et al. (1997) Neuropsychoparmacology 17(4):284-292 for reference values related to measurements for a normal control population (e.g., Table 2 on page 287). In a separate embodiment, elevated AVP may be based on comparison of measured urinary AVP level of a subject collected over a period (such as 24 hours) to the mean urinary AVP level and its standard deviation collected over the same duration for a reference normal population.

In one embodiment, a subject is said to have an elevated AVP if the plasma AVP level of the subject is at least one standard deviation from the mean plasma AVP value (for example, determined in pg/ml; mean plasma AVP value plus one standard deviation) for a normal control population. In another embodiment, the subject is said to have an elevated AVP if the plasma AVP level of the subject is greater than the mean plasma AVP value for a normal control population by at least 1.5 standard deviations. In another embodiment, the subject is said to have an elevated AVP if the plasma AVP level of the subject is greater than the mean plasma AVP value for a normal control population by at least two standard deviations. In another embodiment, the subject is said to have an elevated AVP if the plasma AVP level of the subject is greater than the mean plasma AVP value for a normal control population by at least 2.5 standard deviations. In another embodiment, the subject is said to have an elevated AVP if the plasma AVP level of the subject is greater than the mean plasma AVP value for a normal control population by at least three standard deviations. In another embodiment, the subject is said to have an elevated AVP if the plasma AVP level of the subject is greater than the mean plasma AVP value for a normal control population by at least 3.5 standard deviations. In another embodiment, the subject is said to have an elevated AVP if the plasma AVP level of the subject is greater than the mean plasma AVP value for a normal control population by at least four standard deviations. In another embodiment, the subject is said to have an elevated AVP if the plasma AVP level of the subject is greater than the mean plasma AVP value for a normal population and is between 2.5 and 6 standard deviations from the mean plasma AVP value for a normal control population.

In one embodiment, a subject is said to have an elevated AVP if the urinary AVP level of the subject is at least one standard deviation from the mean urinary AVP value (mean plus one standard deviation) for a normal control population. In another embodiment, the subject is said to have an elevated AVP if the urinary AVP level of the subject is greater than the mean urinary AVP value for a normal control population by at least 1.5 standard deviations. In another embodiment, the subject is said to have an elevated AVP if the urinary AVP level of the subject is greater than the mean urinary AVP value for a normal control population by at least two standard deviations. In another embodiment, the subject is said to have an elevated AVP if the urinary AVP level of the subject is greater than the mean urinary AVP value for a normal control population by at least 2.5 standard deviations. In another embodiment, the subject is said to have an elevated AVP if the urinary AVP level of the subject is greater than the mean urinary AVP value for a normal control population by at least three standard deviations. In another embodiment, the subject is said to have an elevated AVP if the urinary AVP level of the subject is greater than the mean urinary AVP value for a normal control population by at least 3.5 standard deviations. In another embodiment, the subject is said to have an elevated AVP if the urinary AVP level of the subject is greater than the mean urinary AVP value for a normal control population by at least four standard deviations. In another embodiment, the subject is said to have an elevated AVP if the urinary AVP level of the subject is greater than the mean urinary AVP value for a normal population and is between 2.5 and 6 standard deviations from the mean urinary AVP value for a normal control population.

In a separate embodiment, ADPKD is associated with reduced or altered activity of PKD1 protein and/or PKD2 protein. In an embodiment, ADPKD is associated with increased renal epithelial cell proliferation. In another embodiment, ADPKD is associated with bilateral renal enlargement and cyst.

In an embodiment, treating kidney disease comprises inhibiting AVP production in the subject. In an embodiment, inhibiting AVP production lowers AVP plasma level in the subject. In a separate embodiment, lowered AVP plasma level in the subject may be detected as a lower urinary AVP concentration or excretion by the subject.

In some instances, treating ADPKD comprises slowing down the progression of the disease. In an embodiment, treating kidney disease comprises slowing down progression of the cystic disease. Slowing down the progression of the disease does not eliminate the disease but it can result in the subject not developing kidney failure and/or end-stage renal disease during their lifetime. In an embodiment, slowing down progression of the disease or of the cystic disease comprises reducing risk of developing kidney failure and/or end-stage renal disease. In another embodiment, slowing down progression of the disease or of the cystic disease comprises preventing an increase in the number of renal cysts, increase in size of renal cyst, and/or increase in size or mass of one or both kidneys. In another embodiment, slowing down progression of the disease or of the cystic disease comprises reducing number of renal cysts, reducing size of renal cyst, and/or reducing size or mass of one or both kidneys.

In an embodiment, treating kidney disease comprises reducing cAMP production in renal collecting duct cells of the subject. In an embodiment, the renal collecting duct cell is or comprises a principal cell. In an embodiment, treating kidney disease increases urine output and/or decreases urine osmolarity. In an embodiment, treating kidney disease inhibits proliferation of renal epithelial cell.

In an embodiment, treating a disease or a kidney disease associated with elevated AVP in a subject comprises lowering level of circulating AVP in the subject.

In an embodiment, the subject is a mammal. In an embodiment, the mammal is a human, non-human primate, rabbit, sheep, rat, dog, cat, pig, or mouse. In an embodiment, the subject is a human, non-human primate, rabbit, sheep, rat, dog, cat, pig, or mouse. Non-human primate includes but not limited to monkey, chimpanzee, gorilla, ape, lemur, macaque and gibbon. In a preferred embodiment, the non-human primate is a monkey or a chimpanzee. In some instances, the subject is a human. In some instances, the subject has been diagnosed with a need for treatment of ADPKD prior to the administering step. The subject may be in need of treatment of a kidney disease. Thus, the disclosed methods can, in some instances, further comprise the step of identifying a subject in need of treatment of ADPKD. Identifying a subject in need of treatment of ADPKD can comprise ultrasound, CT, or MRI scans to check for kidney abnormality or blood tests to analyze known genetic defects related to ADPKD.

Disclosed are methods for treating autosomal dominant polycystic kidney disease (ADPKD) in a subject, comprising the step of administering to the subject a composition comprising a therapeutically effective amount of ticagrelor or a derivative thereof, thereby treating ADPKD, wherein treating ADPKD comprises reducing cyst number and/or size or decreasing or preventing the increase of kidney size. Other symptoms of ADPKD can be affected during treatment with the disclosed compositions. Other treatable symptoms include, but are not limited to, size of abdomen, presence of kidney stones, high blood pressure, blood in the urine, urinary tract infections, gradual decrease in kidney function, and back and neck pain.

In an embodiment, the subject is free of a coagulation disorder. In an embodiment, the coagulation disorder is a hypercoagulation disorder or thrombophilia. In an embodiment, the hypercoagulation disorder or thrombophilia is inherited hypercoagulable condition. In an embodiment, the inherited hypercoagulable condition is associated with and may include any of factor V Leiden mutation, prothrombin gene mutation, antithrombin III deficiency, protein C deficiency, protein S deficiency, elevated homocysteine level, elevated fibrinogen level, dysfibrinogenemia, elevated factor VIII level, factor XIII mutation, elevated factor IX level, elevated factor XI level, fibrinolysis disorder, plasminogen deficiency and elevated plasminogen activator inhibitor (PAI-1).

In an embodiment, coagulation disorder is a bleeding disorder. In an embodiment, the bleeding disorder is congenital. The congenital bleeding disorder may include any of hemophilia, factor II deficiency, factor V deficiency, factor VII deficiency, factor X deficiency, factor XI deficiency, factor XII deficiency, factor XIII deficiency, von Willebrand's disease, Bernard-Soulier syndrome, complete plasminogen activator inhibitor 1 (PAI-1) deficiency, congenital afrinogenemia, glycoprotein VI deficiency, gray platelet syndrome, Noonan syndrome, prekallikrein deficiency, prothrombin deficiency, Stormorken syndrome, thrombocytopenia-absent radius (TAR) syndrome and Wiskott-Aldrich syndrome.

In an embodiment, diagnosis of ADPKD comprises one or more of large echogenic kidneys without distinct macroscopic cysts at 50% risk for ADPKD, presence of bilateral renal enlargement and cysts, PKD1 gene mutation, PKD2 gene mutation, and mutation in modifiers of PKD1 expression or PKD2 expression.

In an embodiment, treating ADPKD comprises reducing cyst number or size or decreasing kidney size. In an embodiment, the method further comprises ameliorating one or more symptoms associated with ADPKD. In an embodiment, one or more symptoms associated with ADPKD may include any of acute loin pain, haematuria, ballotable kidneys, sub arachnoid hemorrhage (berry aneurysm), hypertension, associated liver cyst, uremia due to renal failure, anemia due to CKD, increase RBC or erythropoeitin secretion.

The disclosed methods can further comprise administering one or more additional therapeutics. Thus, in some instances, disclosed are methods for treating ADPKD in a subject, comprising the step of administering to the subject a composition comprising a therapeutically effective amount of ticagrelor or a derivative thereof, thereby treating ADPKD, further comprising administering one or more additional therapeutic. In some instances, the one or more additional therapeutic is a mTOR inhibitor, such as but not limited to, Sirolimus, Everolimus (RAD001), Temsirolimus (CCI-779), Ridaforolimus (AP23573, MK-8669), Deforolimus, Dactolisib, BGT226, SF1126, PKI-587, Sapanisertib (INK128), AZD8055 and AZD2014. In a preferred embodiment, the mTOR inhibitor may include any of Sirolimus and Everolimus. In some instances, the one or more additional therapeutic is a somatostatin analogue, such as but not limited to, Octreotide, Pasireotide (SOM230), dopastatin BIM-23A387, dopastatin BIM-23A760, somatostatin octapeptide-doxorubicin RC-121, somatostatin octapeptide-doxorubicin RC-160, somatostatin octapeptide-2-pyrrolino-DOX conjugate AN-201, AN-238 (AN-201 linked to RC-121), JF-10-81, 90Y-DOTATOC, 177Lu DOTATATE [177Lu]DOTA-Tyr(3)-octreotate and Lanreotide. In a preferred embodiment, the somatostatin analogue may include any of Octreotide and Lanreotide. In some instances, the one or more additional therapeutic is a vasopressin V2 receptor antagonist, such as but not limited to, OPC-31260, Lixivaptan, Mozavaptan, Satavaptan, Lixivaptan, Conivaptan (YM-087), SR-121463A, VPA-985 and Tolvaptan (OPC-41061). In a preferred embodiment, the vasopressin V2 receptor antagonist may include any of OPC-31260 and Tolvaptan. In some instances, the one or more additional therapeutic is an epidermal growth factor receptor (EGFR) inhibitor, such as but not limited to, bosutinib, gefitinib, lapatinib, cetuximab, panitumumab, vandetanib, neratinib, necitumumab, osimertnib and erlotinib. In a preferred embodiment, the epidermal growth factor receptor (EGFR) inhibitor may include any of bosutinib, gefitinib and erlotinib. A combination of mTOR inhibitors, somatostatin analogues, vasopressin V2 receptor antagonists and EGFR inhibitors can be used. In some instances, the one or more additional therapeutic can be administered in the same composition or in a separate composition as the ticagrelor. In some instances, the additional therapeutic can be administered simultaneously or consecutively with the ticagrelor.

In an embodiment, the one or more additional therapeutic is administered concurrently or sequentially with ticagrelor or its derivative. In an embodiment, the one or more additional therapeutic is administered before, after or taken with a composition comprising ticagrelor or its derivative. In an embodiment, the composition comprising ticagrelor or its derivative is administered orally, intravenously, subcutaneously or intramuscularly, as an implant or patch, or via a needle or microneedles. In one embodiment, the one or more additional therapeutic is administered orally, intravenously, subcutaneously or intramuscularly, or as an implant or patch, or via a needle or microneedles.

In one embodiment, one or more additional therapeutic is administered by the same route as a composition comprising ticagrelor or its derivative. In another embodiment, one or more additional therapeutic is administered by a different route as a composition comprising ticagrelor or its derivative. Disclosed are methods for treating ADPKD in a subject comprising the step of administering to the subject a composition comprising a therapeutically effective amount of ticagrelor or a derivative thereof, thereby treating ADPKD, wherein the step of administering to the subject a composition comprising an effective amount of ticagrelor is a long-term treatment regimen. A long-term treatment regimen or chronic treatment regimen means a course of treatment that lasts longer than 1 month to a life-time depending on the subject. Typically, in a laboratory or experimental animal, such as a mouse, long-term treatment regimen or chronic treatment regimen in such a subject may be measured in months, such as lasting longer than 1, 2, 3, 4, 5, 6, 7, 8, 9, 10, 11, or 12 months. Typically, in human subjects or patients, long-term treatment regimen or chronic treatment regimen may be measured in years, such as lasting longer than 1, 2, 3, 4, 5, 6, 7, 8, 9, 10, 15, 20, 25, or 30 years. In some instances, the long-term treatment regimen lasts a lifetime.

In an embodiment, the step of administering to the subject a composition comprising an effective amount of ticagrelor is a long-term treatment regimen. In an embodiment, the long-term treatment regimen is at least 2 weeks. In a different embodiment, the long-term treatment regimen is at least 1 month. In another embodiment, the long-term treatment regimen is at least 1 year. In another embodiment, the long-term treatment regimen is at least 5 years. In a further embodiment, the long-term treatment regimen is a lifetime from a diagnosis of need to treat.

In an embodiment, the long-term treatment is continuous. In a different embodiment, the long-term treatment is discontinuous, wherein the treatment is interrupted by one or more period in which administration of the composition comprising an effective amount of ticagrelor or its derivative is withheld.

In an embodiment, withholding a composition comprising an effective amount of ticagrelor or its derivative is for a sufficient amount of time or for a specified amount of time. In another embodiment, withholding a composition comprising an effective amount of ticagrelor or its derivative is for a sufficient amount of time in which withholding inhibits or reverses uncontrolled bleeding from the wound or internal ulcer. In an embodiment, withholding a composition comprising an effective amount of ticagrelor or its derivative for a specified amount of time reduces risk of uncontrolled bleeding associated with a procedure or therapy. In an embodiment, the procedure is surgery or intervention radiology. In an embodiment, the therapy increases bleeding time or decreases clotting time so as to place the subject at risk for uncontrolled bleeding.

In an embodiment, decrease in AVP production is determined by comparing AVP levels detected in the blood or urine of the subject before administering ticagrelor or its derivative to AVP levels detected in the blood or urine of the subject after administering ticagrelor or its derivative. In an embodiment, AVP levels detected in the blood or urine of the subject after administering ticagrelor are detected at least one week after administering ticagrelor.

In some instances, the dose of tricagrelor can be 50, 60, 70, 80, 90, 100, 110, 120, 130, 140, 150 mg twice per day. In some instances, the same daily dose is received in a once per day form. In some instances, tricagrelor can be taken daily, weekly, or monthly.

Methods for Treating Disease Associated with Elevated AVP

Disclosed are methods for treating for treating a disease associated with elevated AVP in a subject suffering therefrom, comprising the step of administering to the subject a composition comprising a therapeutically effective amount of ticagrelor or a derivative thereof, thereby treating the disease in the subject.

In an embodiment, the disease may include any of hypertension, preeclampsia, congestive heart failure, cardiorenal syndrome, cirrhosis of liver, diabetic ketoacidosis, post-traumatic stress disorder (PTSD), countering effect of loop diuretics, high altitude pulmonary edema, autism, syndrome of inappropriate antidiuretic hormone (SIADH), autosomal dominant polycystic kidney disease (ADPKD), dilutional hyponatremia and disease associated with elevated activity of AVP-V2 receptor-cAMP axis. In some instances, autism may be autism spectrum disorder (ASD).

In an embodiment, elevated activity of AVP-V2 receptor-cAMP axis comprises elevated circulating AVP and/or elevated V2 receptor signaling in the subject. In an embodiment, elevated V2 receptor signaling comprises elevated cAMP level in a V2 receptor positive cell of the subject.

In an embodiment, V2 receptor positive cell is a renal collecting duct cell. In an embodiment, the renal collecting duct cell comprises a principal cell. In an embodiment, the renal collecting duct cell is a principal cell. In an embodiment, the renal collecting duct cell is a renal epithelial cell. In an embodiment, the renal epithelial cell is a principal cell of the collecting duct. In an embodiment, the principal cell translocates aquaporin protein to apical plasma membrane. In a separate embodiment, the aquaporin protein is in a subapical vesicle prior to transport to apical plasma membrane. In an embodiment, the principal cell increases expression of aquaporin gene. Aquaporin may be aquaporin protein 2 (AQP2) and aquaporin protein 3 (AQP3).

In an embodiment, translocation of aquaporin and/or increased expression of aquaporin gene alters transepithelial water transport. In an embodiment, alteration of transepithelial water transport comprises increased re-absorption of water by the principal cell or renal collecting duct cell, decreased urine output, increased urine osmolarity, and/or increased urinary AVP excretion. In an embodiment, increased urinary AVP excretion positively correlates with an increased plasma AVP level.

In an embodiment, treating the disease in the subject comprises inhibiting AVP production in hypothalamus. In another embodiment, treating the disease in the subject comprises lowering circulating level of AVP in the subject. In an embodiment, lowering circulating level of AVP reduces signaling by AVP-dependent V2 receptor in a cell of the subject. In an embodiment, reducing signaling by AVP-dependent V2 receptor decreases cAMP levels in the cell of the subject. In another embodiment, lowering circulating level of AVP reduces signaling by AVP-dependent V1 receptor in a cell of the subject. In an embodiment, reducing signaling by AVP-dependent V1 receptor decreases intracellular calcium in a cell of the subject. V1a receptor may be V1a receptor or V1b receptor. In an embodiment, reducing signaling by AVP-dependent V1 or V2 receptor slows or reverses a disease associated with elevated AVP in the subject.

In an embodiment, the cell of the subject is a renal collecting duct cell. In an embodiment, the renal collecting duct cell may be a renal epithelial cell. In an embodiment, the renal collecting duct cell is or comprises a principal cell.

In an embodiment, the principal cell has a lower cAMP level. In an embodiment, the renal collecting duct cell has a lower cAMP level. In an embodiment, the renal epithelial cell has a lower cAMP level. Such a lower cAMP may be due to lower plasma level of AVP, such that second messenger signaling through production of cAMP by AVP-dependent receptor is decreased. In a preferred embodiment, AVP-dependent receptor in principal cell, renal epithelial cell or renal collecting duct cell is V2 receptor or vasopressin V2 receptor.

In an embodiment, lowering of cAMP level results in a decrease number of aquaporin proteins on apical surface of the principal cell. In an embodiment, lowering of cAMP level results in a decreased expression of aquaporin genes. In an embodiment, aquaporin proteins may include any of aquaporin protein 2 (AQP2) and aquaporin protein 3 (AQP3). In a preferred embodiment, aquaporin protein is aquaporin protein 2 (AQP2).

In an embodiment, decreased number of aquaporin proteins on apical surface of the principal cell result in a decreased re-absorption of water by the principal cell or renal collecting duct cell, increased urine output, decreased urine osmolarity, and/or decreased urinary AVP excretion. In an embodiment, decreased urinary AVP excretion positively correlates with a decreased plasma AVP level.

In an embodiment, treating a disease or a kidney disease associated with elevated AVP in a subject comprises lowering level of circulating AVP in the subject. In an embodiment, the subject may be in need of treatment of a kidney disease.

In an embodiment, the subject is free of a coagulation disorder. In an embodiment, the coagulation disorder may be a hypercoagulation disorder or thrombophilia. In an embodiment, the hypercoagulation disorder or thrombophilia may be inherited hypercoagulable condition. In an embodiment, the inherited hypercoagulable condition may be associated with and may include any of factor V Leiden mutation, prothrombin gene mutation, antithrombin III deficiency, protein C deficiency, protein S deficiency, elevated homocysteine level, elevated fibrinogen level, dysfibrinogenemia, elevated factor VIII level, factor XIII mutation, elevated factor IX level, elevated factor XI level, fibrinolysis disorder, plasminogen deficiency and elevated plasminogen activator inhibitor (PAI-1).

In an embodiment, coagulation disorder may be a bleeding disorder. In an embodiment, the bleeding disorder may be congenital. the congenital bleeding disorder may include any of hemophilia, factor II deficiency, factor V deficiency, factor VII deficiency, factor X deficiency, factor XI deficiency, factor XII deficiency, factor XIII deficiency, von Willebrand's disease, Bernard-Soulier syndrome, complete plasminogen activator inhibitor 1 (PAI-1) deficiency, congenital afrinogenemia, glycoprotein VI deficiency, gray platelet syndrome, Noonan syndrome, prekallikrein deficiency, prothrombin deficiency, Stormorken syndrome, thrombocytopenia-absent radius (TAR) syndrome and Wiskott-Aldrich syndrome.

In an embodiment, the method further comprises ameliorating one or more symptoms associated with ADPKD. In an embodiment, one or more symptoms associated with ADPKD may include any of acute loin pain, haematuria, ballotable kidneys, sub arachnoid hemorrhage (berry aneurysm), hypertension, associated liver cyst, uremia due to renal failure, anemia due to CKD, increase RBC or erythropoeitin secretion.

In an embodiment, the method further comprises administering one or more additional therapeutic.

In an embodiment, the one or more additional therapeutic may be a mTOR inhibitor. In an embodiment, mTOR inhibitor may include any of Sirolimus, Everolimus (RAD001), Temsirolimus (CCI-779), Ridaforolimus (AP23573, MK-8669), Deforolimus, Dactolisib, BGT226, SF1126, PKI-587, Sapanisertib (INK128), AZD8055 and AZD2014. In a preferred embodiment, mTOR inhibitor may include any of Sirolimus and Everolimus (RAD001).

In an embodiment, the one or more additional therapeutic may be a somatostatin analogue. In an embodiment, the somatostatin analogue may include any of Octreotide, Pasireotide (SOM230), dopastatin BIM-23A387, dopastatin BIM-23A760, somatostatin octapeptide-doxorubicin RC-121, somatostatin octapeptide-doxorubicin RC-160, somatostatin octapeptide-2-pyrrolino-DOX conjugate AN-201, AN-238 (AN-201 linked to RC-121), JF-10-81, $^{90}$Y-DOTATOC, 177Lu DOTATATE [177Lu]DOTA-Tyr(3)-octreotate and Lanreotide. In a preferred embodiment, the somatostatin analogue may include any of Octreotide and Lanreotide.

In an embodiment, the one or more additional therapeutic is a vasopressin V2 receptor antagonist. In an embodiment, the vasopressin V2 receptor antagonist may include any of OPC-31260, Lixivaptan, Mozavaptan, Satavaptan, Lixivaptan, Conivaptan (YM-087), SR-121463A, VPA-985 and Tolvaptan (OPC-41061). In a preferred embodiment, the vasopressin V2 receptor antagonist may include any of OPC-31260 and Tolvaptan.

In an embodiment, the one or more additional therapeutic may be an epidermal growth factor receptor inhibitor. In an embodiment, the epidermal growth factor receptor inhibitor may include any bosutinib, gefitinib, lapatinib, cetuximab, panitumumab, vandetanib, neratinib, necitumumab, osimertnib and erlotinib. In a preferred embodiment, the epidermal growth factor receptor inhibitor may include any of bosutinib, gefitinib and erlotinib.

In an embodiment, the one or more additional therapeutic may be administered concurrently or sequentially with ticagrelor or its derivative. In an embodiment, the one or more additional therapeutic may be administered before, after or taken with a composition comprising ticagrelor or its derivative. In an embodiment, the composition comprising ticagrelor or its derivative may be administered orally, intravenously, subcutaneously or intramuscularly, as an implant or patch, or via a needle or microneedles. In one embodiment, the one or more additional therapeutic may be administered orally, intravenously, subcutaneously or intramuscularly, or as an implant or patch, or via a needle or microneedles.

In one embodiment, one or more additional therapeutic may be administered by the same route as a composition comprising ticagrelor or its derivative. In another embodiment, one or more additional therapeutic may be administered by a different route as a composition comprising ticagrelor or its derivative.

In an embodiment, the step of administering to the subject a composition comprising an effective amount of ticagrelor may be a long-term treatment regimen. In an embodiment, the long-term treatment regimen may be at least 2 weeks. In a different embodiment, the long-term treatment regimen may be at least 1 month. In another embodiment, the long-term treatment regimen may be at least 1 year. In another embodiment, the long-term treatment regimen is at least 5 years. In a further embodiment, the long-term treatment regimen may be a lifetime from a diagnosis of need to treat.

In an embodiment, the long-term treatment is continuous. In a different embodiment, the long-term treatment is discontinuous, wherein the treatment may be interrupted by one or more period in which administration of the composition comprising an effective amount of ticagrelor or its derivative is withheld.

In an embodiment, withholding a composition comprising an effective amount of ticagrelor or its derivative may be for a sufficient amount of time or for a specified amount of time. In another embodiment, withholding a composition comprising an effective amount of ticagrelor or its derivative may be for a sufficient amount of time in which withholding inhibits or reverses uncontrolled bleeding from the wound or internal ulcer. In an embodiment, withholding a composition comprising an effective amount of ticagrelor or its derivative for a specified amount of time may reduce risk of uncontrolled bleeding associated with a procedure or therapy. In an embodiment, the procedure may be surgery or intervention radiology. In an embodiment, the therapy increases bleeding time or decreases clotting time so as to place the subject at risk for uncontrolled bleeding.

In an embodiment, decrease in AVP production may be determined by comparing AVP levels detected in the blood or urine of the subject before administering ticagrelor or its derivative to AVP levels detected in the blood or urine of the subject after administering ticagrelor or its derivative. In an embodiment, AVP levels detected in the blood or urine of the subject after administering ticagrelor may be detected at least one week after administering ticagrelor.

In some instances, the dose of tricagrelor can be 50, 60, 70, 80, 90, 100, 110, 120, 130, 140, 150 mg twice per day.

In some instances, the same daily dose may be received in a once per day form. In some instances, tricagrelor can be taken daily, weekly, or monthly.

Methods of Decreasing Arginine Vasopressin (AVP) Production

Disclosed are methods of decreasing arginine vasopressin (AVP) production in a subject comprising the step of administering to the subject a composition comprising an effective amount of ticagrelor, thereby decreasing AVP production. In some instances, the decrease in AVP production can be determined by comparing AVP levels detected in the blood or urine of the subject before administering ticagrelor to AVP levels detected in the blood or urine of the subject after administering ticagrelor. AVP levels in the urine can correlate to the levels in the plasma, therefore using urine or blood samples for detection of AVP levels can be appropriate.

In some instances, AVP levels detected in the blood or urine of the subject after administering daily doses of ticagrelor can be detected at least one week after administering ticagrelor. In some instances, AVP levels can be detected, 1, 2, 3, 4, 5, 6, 7, 8, 9, 10, 11, 12, 13, or 14 days after administering ticagrelor. In some instances, AVP levels can be detected 2, 4, 6, 7, 8, 10, or 12 weeks after administering daily doses of ticagrelor.

The method may include methods disclosed elsewhere in the application.

Methods for Treating Dilutional Hyponatremia

Hyponatremia is a disorder characterized by an excess of body water relative to body content of sodium. Hyponatremia is the most common electrolyte disorder encountered in hospitalized patients (25-30%), associated with increased morbidity and mortality. Hyponatremia also represents a huge economic burden on the health care system, typically costing $10,000 more per hospitalized patient, over other hospitalized patients that do not have hyponatremia. It is often seen in patients with congestive heart failure (CHF), cirrhosis of liver and in SIADH (syndrome of inappropriate anti-diuretic hormone secretion) among others. In these conditions, the plasma levels of AVP are inappropriately high.

Disclosed are methods for treating dilutional hyponatremia in a subject comprising the step of administering to the subject a composition comprising an effective amount of ticagrelor, thereby decreasing AVP production.

Disclosed are methods for treating dilutional hyponatremia in a subject comprising the step of administering to the subject a composition comprising an effective amount of ticagrelor, thereby decreasing AVP production, further comprising ameliorating one or more symptoms associated with dilutional hyponatremia. In some instances, one or more symptom associated with dilutional hyponatremia can be, but is not limited to fatigue, headache, muscle spasms, muscle cramps, confusion or hallucination.

Disclosed are methods for treating dilutional hyponatremia in a subject comprising the step of administering to the subject a composition comprising an effective amount of ticagrelor, thereby decreasing AVP production, further comprising administering an additional therapeutic. In some instances, the additional therapeutic is tolvaptan, a known vasopressin V2 receptor antagonist for treating hyponatremia. In some instances, the additional therapeutic can be administered in the same composition or in a separate composition. In some instances, the additional therapeutic can be administered simultaneously or consecutively with the ticagrelor.

In an embodiment, the method further comprises ameliorating one or more symptoms associated with dilutional hyponatremia. The method may further comprise administering an additional therapeutic, in addition to a composition comprising an effective amount of ticagrelor or a derivative thereof. In an embodiment, the additional therapeutic is a vasopressin V2 receptor antagonist. In an embodiment, vasopressin V2 receptor antagonist may include any of OPC-31260, Lixivaptan, Mozavaptan, Satavaptan, Lixivaptan, Conivaptan (YM-087), SR-121463A, VPA-985 and Tolvaptan (OPC-41061). In a preferred embodiment, the vasopressin V2 receptor antagonist is tolvaptan.

In an embodiment, the subject is a mammal. In an embodiment, the mammal is a human, non-human primate, rabbit, sheep, rat, dog, cat, pig, or mouse. Non-human primate includes but not limited to monkey, chimpanzee, gorilla, ape, lemur, macaque and gibbon. In a preferred embodiment, the non-human primate is a monkey or a chimpanzee.

Methods of Reducing One or More Symptoms Associated with ADPKD

Disclosed are methods of reducing one or more symptoms associated with ADPKD in a subject, comprising the step of administering to the subject a composition comprising an effective amount of ticagrelor or a derivative thereof, so as to reduce circulating levels of AVP, thereby reducing one or more symptoms associated with ADPKD in the subject.

In an embodiment, one or more symptoms associated with ADPKD may include any of acute loin pain, haematuria, ballotable kidneys, sub arachnoid hemorrhage (berry aneurysm), hypertension, associated liver cyst, uremia due to renal failure, anemia due to CKD, increase RBC or erythropoeitin secretion.

In an embodiment, the method further comprises administering one or more additional therapeutic. The additional therapeutic may include any of a mTOR inhibitor, a somastostatin analogue, a vasopressin V2 receptor antagonist and an epidermal growth factor receptor inhibitor. Examples of such therapeutics are provided elsewhere in the application. In an embodiment, the additional therapeutic may include any of Sirolimus, Everolimus (RAD001), Temsirolimus (CCI-779), Ridaforolimus (AP23573, MK-8669), Deforolimus, Dactolisib, BGT226, SF1126, PKI-587, Sapanisertib (INK128), AZD8055, AZD2014, Octreotide, Pasireotide (SOM230), dopastatin BIM-23A387, dopastatin BIM-23A760, somatostatin octapeptide-doxorubicin RC-121, somatostatin octapeptide-doxorubicin RC-160, somatostatin octapeptide-2-pyrrolino-DOX conjugate AN-201, AN-238 (AN-201 linked to RC-121), JF-10-81, $^{90}$Y-DOTATOC, 177Lu DOTATATE [177Lu]DOTA-Tyr(3)-octreotate, Lanreotide, OPC-31260, Lixivaptan, Mozavaptan, Satavaptan, Lixivaptan, Conivaptan (YM-087), SR-121463A, VPA-985 and Tolvaptan (OPC-41061), bosutinib, gefitinib, lapatinib, cetuximab, panitumumab, vandetanib, neratinib, necitumumab, osimertnib and erlotinib. In a preferred embodiment, the additional therapeutic may include any of Sirolimus, Everolimus (RAD001), Octreotide, Lanreotide, OPC-31260, Tolvaptan, bosutinib, gefitinib and erlotinib. In a more preferred embodiment, the additional therapeutic is tolvaptan.

In an embodiment, the subject is a mammal. The mammal may be a human, non-human primate, rabbit, sheep, rat, dog, cat, pig, or mouse. Examples of non-human primate include but not limited to monkey, chimpanzee, gorilla, ape, lemur, macaque and gibbon. In a preferred embodiment, the non-human primate is a monkey or a chimpanzee. In some instances, the subject is a human. In an embodiment, the subject is a human in need of a treatment. In an embodiment, the subject is a human in need of a treatment for symptoms associated with ADPKD or elevated plasma AVP level.

Methods for Treating ADPKD

Disclosed are methods for treating ADPKD in a subject suffering therefrom, comprising the step of administering to the subject a composition comprising a therapeutically effective amount of ticagrelor or a derivative thereof, thereby treating ADPKD in the subject.

In an embodiment, the subject does not have an elevated level of plasma AVP and/or elevated level of urinary AVP. In an embodiment, the subject is free of an elevated level of plasma AVP and/or elevated level of urinary AVP. The subject may be a human, non-human primate, rabbit, sheep, rat, dog, cat, pig, or mouse.

In an embodiment, administering to the subject a composition comprising a therapeutically effective amount of ticagrelor or a derivative thereof comprises reducing cyst number and/or size or decreasing or preventing the increase of kidney size.

In an embodiment, administering to the subject a composition comprising a therapeutically effective amount of ticagrelor or a derivative thereof alleviates or reduces one or more symptoms associated with ADPKD. In an embodiment, the one or more symptoms associated with ADPKD may include any of acute loin pain, haematuria, ballotable kidneys, sub arachnoid hemorrhage (berry aneurysm), hypertension, associated liver cyst, uremia due to renal failure, anemia due to CKD, increase RBC or erythropoeitin secretion. In another embodiment, the one or more symptoms associated with ADPKD may include any of size of abdomen, presence of kidney stones, high blood pressure, blood in the urine, urinary tract infections, gradual decrease in kidney function, and back and neck pain.

In an embodiment, the method further comprises administering one or more additional therapeutic. The additional therapeutic may include any of a mTOR inhibitor, a somastostatin analogue, a vasopressin V2 receptor antagonist and an epidermal growth factor receptor inhibitor. Such inhibitors are described elsewhere in the application.

In an embodiment, the additional therapeutic may include any of Sirolimus, Everolimus (RAD001), Temsirolimus (CCI-779), Ridaforolimus (AP23573, MK-8669), Deforolimus, Dactolisib, BGT226, SF1126, PKI-587, Sapanisertib (INK128), AZD8055, AZD2014, Octreotide, Pasireotide (SOM230), dopastatin BIM-23A387, dopastatin BIM-23A760, somatostatin octapeptide-doxorubicin RC-121, somatostatin octapeptide-doxorubicin RC-160, somatostatin octapeptide-2-pyrrolino-DOX conjugate AN-201, AN-238 (AN-201 linked to RC-121), JF-10-81, 90Y-DOTATOC, 177Lu DOTATATE [177Lu]DOTA-Tyr(3)-octreotate, Lanreotide, OPC-31260, Lixivaptan, Mozavaptan, Satavaptan, Lixivaptan, Conivaptan (YM-087), SR-121463A, VPA-985 and Tolvaptan (OPC-41061), bosutinib, gefitinib, lapatinib, cetuximab, panitumumab, vandetanib, neratinib, necitumumab, osimertnib and erlotinib. In a preferred embodiment, the additional therapeutic may include any of Sirolimus, Everolimus (RAD001), Octreotide, Lanreotide, OPC-31260, Tolvaptan, bosutinib, gefitinib and erlotinib. In a more preferred embodiment, the additional therapeutic may be tolvaptan.

In an embodiment, treating ADPKD in the subject with a composition comprising a therapeutically effective amount of ticagrelor or a derivative thereof, may be a long-term treatment regimen or chronic treatment regimen.

In an embodiment, the long-term treatment regimen is at least 2 weeks. In a different embodiment, the long-term treatment regimen is at least 1 month. In another embodiment, the long-term treatment regimen is at least 1 year. In another embodiment, the long-term treatment regimen is at least 5 years. In a further embodiment, the long-term treatment regimen is a lifetime from a diagnosis of need to treat.

In an embodiment, the long-term treatment may be continuous. In a different embodiment, the long-term treatment may be discontinuous, wherein the treatment may be interrupted by one or more period in which administration of the composition comprising an effective amount of ticagrelor or its derivative is withheld.

In an embodiment, withholding a composition comprising an effective amount of ticagrelor or its derivative may be for a sufficient amount of time or for a specified amount of time.

In an embodiment, ADPKD in a subject suffering therefrom may be treated with a composition comprising a therapeutically effective amount of ticagrelor or a derivative thereof irrespective of coagulation status.

In a separate embodiment, ADPKD in a subject suffering therefrom may be treated with a composition comprising a therapeutically effective amount of ticagrelor or a derivative thereof taking into consideration coagulation status.

In an embodiment, the subject may be free of a coagulation disorder. In an embodiment, the coagulation disorder may be a hypercoagulation disorder or thrombophilia.

In an embodiment, the hypercoagulation disorder or thrombophilia may be inherited hypercoagulable condition. In an embodiment, the inherited hypercoagulable condition may be associated with and may include any of factor V Leiden mutation, prothrombin gene mutation, antithrombin III deficiency, protein C deficiency, protein S deficiency, elevated homocysteine level, elevated fibrinogen level, dysfibrinogenemia, elevated factor VIII level, factor XIII mutation, elevated factor IX level, elevated factor XI level, fibrinolysis disorder, plasminogen deficiency and elevated plasminogen activator inhibitor (PAI-1).

In an embodiment, coagulation disorder may be a bleeding disorder. In an embodiment, the bleeding disorder may be congenital. The congenital bleeding disorder may include any of hemophilia, factor II deficiency, factor V deficiency, factor VII deficiency, factor X deficiency, factor XI deficiency, factor XII deficiency, factor XIII deficiency, von Willebrand's disease, Bernard-Soulier syndrome, complete plasminogen activator inhibitor 1 (PAI-1) deficiency, congenital afrinogenemia, glycoprotein VI deficiency, gray platelet syndrome, Noonan syndrome, prekallikrein deficiency, prothrombin deficiency, Stormorken syndrome, thrombocytopenia-absent radius (TAR) syndrome and Wiskott-Aldrich syndrome.

In an embodiment, the subject has a hypercoagulation disorder or thrombophilia and treatment with tricagrelor may treat both ADPKD and its symptoms as well as may reduce or alleviate hypercoagulation disorder or thrombophila. In an embodiment, the hypercoagulation disorder or thrombophilia may be inherited hypercoagulable condition. In an embodiment, the inherited hypercoagulable condition may be associated with and may include any of factor V Leiden mutation, prothrombin gene mutation, antithrombin III deficiency, protein C deficiency, protein S deficiency, elevated homocysteine level, elevated fibrinogen level, dysfibrinogenemia, elevated factor VIII level, factor XIII mutation, elevated factor IX level, elevated factor XI level, fibrinolysis disorder, plasminogen deficiency and elevated plasminogen activator inhibitor (PAI-1).

In some instances, the dose of tricagrelor may be 50, 60, 70, 80, 90, 100, 110, 120, 130, 140, 150 mg twice per day. In some instances, the same daily dose may be received in a once per day form. In some instances, tricagrelor can be taken daily, weekly, or monthly.

Methods of Decreasing Proliferation of Medullary Collecting Duct Cells

Disclosed are methods of decreasing proliferation of medullary collecting duct cells comprising administering to a subject a composition comprising an effective amount of ticagrelor, thereby decreasing proliferation of medullary collecting duct cells. Increasing concentrations of ticagrelor causes a decrease in the proliferation of medullary collecting duct cells.

Compositions and Administration

Disclosed are compositions comprising ticagrelor and derivatives thereof. Examples of derivatives of ticagrelor can be found in U.S. Pat. Nos. 6,525,060 and 6,251,910, both of which are incorporated herein by reference. An examples of a ticagrelor derivatives can be Triazolo[4,5-D] Pyrimidine compounds.

Examples of ticagrelor and derivatives thereof can include compounds having the formula:

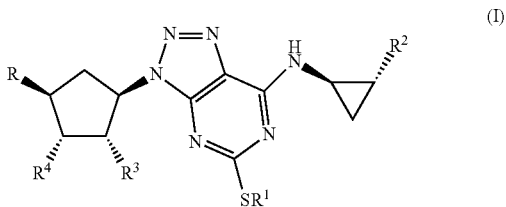

(I)

wherein: R$^1$ is C3-5 alkyl optionally substituted by one or more halogen atoms; R$^2$ is a phenyl group, optionally substituted by one or more fluorine atoms; R$^3$ and R$^4$ are both hydroxy;

R is XOH, where X is CH$_2$, OCH$_2$CH$_2$ or a bond; or a pharmaceutically acceptable salt or solvate thereof, or a solvate of such a salt provided that: when X is CH$_2$ or a bond, R$^1$ is not propyl; when X is CH$_2$ and R$^1$ is CH$_2$CH$_2$CF$_3$, butyl or pentyl, the phenyl group at R$^2$ must be substituted by fluorine; when X is OCH$_2$CH$_2$ and R$^1$ is propyl, the phenyl group at R$^2$ must be substituted by fluorine.

Additional examples of derivatives of ticagrelor, include, but are not limited to, [1R-[1α,2α,3β(1R*,2S*),5]]-3-[7-[[2-(4-Fluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol; [1R-[1α,2α,3β(1R*,2S*),5P]]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(hydroxymethyl)-cyclopentane-1,2-diol; [1 S-(1α,2α,3β(1S*,2R*),5β]]-3-[7-[[2-(3,4-Difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol; 1R-[1α,2α,3β(1R*,2S*),5β]]-3-[5-(Butylthio)-7-[[2-(3,4-difluorophenyl)cyclopropyl]amino]-3H-1,2,3-triazolo[4,5-d]pyrimidin-3-yl]-5-(hydroxymethyl)-cyclopentane-1,2-diol; [1S-[1α,2β,3β,4α(1S*,2R*)]]-4-[5-(Butylthio)-7-[[2-(4-fluorophenyl)cyclopropyl]amino]-3H-1,2,3-triazolo[4,5-d]pyrimidin-3-yl]-cyclopentane-1,2,3-triol; [1S-(1α,2α,3β(1S*,2R*),5]-3-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-5-(2-hydroxyethoxy)-cyclopentane-1,2-diol; [1 S-[1α,2α,3β,5β(1S*,2R*)]]-3-(2-Hydroxyethoxy)-5-[7-(2-phenylcyclopropyl)amino]-5-[(3,3,3-trifluoropropyl)thio]-3H-1,2,3-triazolo[4,5-d]pyrimidin-3-yl]-cyclopentane-1,2-diol[1S-[1α,2β,3β,4α(1S*,2R*)]]-4-[5-(Butylthio)-7-[[2-(3,4-difluorophenyl)cyclopropyl]amino]-3H-1,2,3-triazolo[4,5-d]pyrimidin-3-yl]cyclopentane-1,2,3-triol; [1S-[1α,2α,3β(1S*,2R*),53]]-3-[5-(Butylthio)-7-[(2-phenylcyclopropyl)amino]-3H-1,2,3-triazolo[4,5-d]pyrimidin-3-yl]-5-(2-hydroxethoxy)-cyclopentane-1,2-diol; or pharmaceutically acceptable salts or solvates thereof, or solvates of such salts.

Alkyl groups, whether alone or as part of another group are straight chained and fully saturated.

Additional examples of derivatives of ticagrelor, include, but are not limited to, [3aR-[3aα,4α,6α(1R*,2S*),6aα]]-6-[7-[[2-(4-Fluorophenyl)cyclopropyl]amino]-5-(propylsulphonyl)-3H-1,2,3-triazolo[4,5-d]pyrimidin-3-yl]-tetrahydro-2,2-dimethyl-4H-cyclopenta-1,3-dioxole-4-methanol; [[3aR-[3aα,4α,6α(1R*,2S*),6aα]]-6-[7-[[2-(4-Fluorophenyl)cyclopropyl]amino]-5-[(3,3,3-trifluoropropyl)thio]-3H-1,2,3-triazolo[4,5-d]pyrimidin-3-yl]-tetrahydro-2,2-dimethyl-4H-cyclopenta-1,3-dioxole-4-methanol; [3aR-[3aα,4α,6α(1R*,2S*),6aα]]-6-[7-[[2-(3,4-Difluorophenyl)cyclopropyl]amino]-5-[(3,3,3-trifluoropropyl)thio]-3H-1,2,3-triazolo[4,5-d]pyrimidin-3-yl]-tetrahydro-2,2-dimethyl-4H-cyclopenta-1,3-dioxole-4-methanol; [3aR-(3aα,4α,6α,6aα)]-6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol; [3aR-(3aα,4α,6α,6aα)]-[[6-[7-Amino-5-(propylthio)-3H-1,2,3-triazolo[4,5-d]-pyrimidin-3-yl]-tetrahydro-2,2-dimethyl-4H-cyclopenta-1,3-dioxol-4-ol]oxy]acetic acid, methyl ester; [3aR-(3aα,4α,6α,6aα)]-[[6-[7-Bromo-5-(propylthio)-3H-1,2,3-triazolo[4,5-d]-pyrimidin-3-yl]-tetrahydro-2,2-dimethyl-4H-cyclopenta-1,3-dioxol-4-ol]oxy] acetic acid, methyl ester; [3aR-[3aα,4α,6α(1 R*,2S*),6aα]]-[[6-[7-[[2-(3,4-Difluorophenyl)cyclopropyl]amino]-5-(propylthio)-3H-1,2,3-triazolo[4,5-d]-pyrimidin-3-yl]-tetrahydro-2,2-dimethyl-4H-cyclopenta-1,3-dioxol-4-yl]oxy]acetic acid, methyl ester; [3aR-[3aα,4α,6α(1R*,2S*),6aα]]-6-[[7-[2-(3,4-Difluorophenyl)cyclopropyl]amino-5-(propylthio)-3H-1,2,3-triazolo[4,5-d]pyrimidin-3-yl]-tetrahydro-2,2-dimethyl-4H-cyclopenta-1,3-dioxol-4-yl] oxy]-ethanol; [3aR-(3aα,4α,6α,6aα)]-6-[7-Amino-5-(propylthio)-3H-1,2,3-triazolo[4,5-d]pyrimidin-3-yl]-tetrahydro-2,2-dimethyl-4H-cyclopenta-1,3-dioxole-4-methanol; [3aR-(3aα,4α,6α,6aα)]-6-[7-Amino-5-(propylsulfonyl)-3H-1,2,3-triazolo[4,5-d]pyrimidin-3-yl]-tetrahydro-2,2-dimethyl-4H-cyclopenta-1,3-dioxole-4-methanol; [3aR-(3aα,4α,6α,6aα)]-6-[7-Amino-5-(butylthio)-3H-1,2,3-triazolo[4,5-d]pyrimidin-3-yl]-tetrahydro-2,2-dimethyl-4H-cyclopenta-1,3-dioxole-4-methanol; [3aR-(3aα,4α,6α,6aα)]-6-[7-Amino-5-(butylthio)-3H-1,2,3-triazolo[4,5-d]pyrimidin-3-yl]-tetrahydro-2,2-dimethyl-4H-cyclopenta-1,3-dioxole-4-methanol, acetate; [3aR-(3aα,4α,6α,6aα)]-6-[7-Bromo-5-(butylthio)-3H-1,2,3-triazolo[4,5-d]pyrimidin-3-yl]-tetrahydro-2,2-dimethyl-4H-cyclopenta-1,3-dioxole-4-methanol, acetate; [3aR-[3aα,4α,6α(1R*,2S*),6aα]]-6-[5-(Butylthio)-7-[[2-(3,4-difluorophenyl)cyclopropyl]amino]-3H-1,2,3-triazolo[4,5-d]pyrimidin-3-yl]-tetrahydro-2,2-dimethyl-4H-cyclopenta-1,3-dioxole-4-methanol, acetate; [3aR-[3aα,4α,6α,6aα(1 S*,2R*)]]-6-[7-[[(4-Fluorophenyl)cyclopropyl]amino]-5-(propylthio)-3H-1,2,3-triazolo[4,5-d]pyrimdin-3-yl]-tetrahydro-2,2-dimethyl-4H-cyclopenta-1,3-dioxol-4-ol; [3aR-[3aα,4α,6α,6aα(1 S*,2R*)]]-6-[[7-[(4-Fluorophenyl)cyclopropyl]amino]-5-(propylsulphonyl)-3H-1,2,3-triazolo[4,5-d]pyrimidin-3-yl]-tetrahydro-2,2-dimethyl-4H-cyclopenta-1,3-dioxol-4-ol; [3aR-[3aα,4α,6α,6aα(1S*,2*]]-6-[7-[[(4-Fluorophenyl)cyclopropyl]amino]-

5-(butylthio)-3H-1,2,3-triazolo[4,5-d]pyrimidin-3-yl]-tetrahydro-2,2-dimethyl-4H-cyclopenta-1,3-dioxol-4-ol; [1S-(1α, 2α, 3β(1S*,2*),5β)]-3-[7-[[2-(3,4Difluorophenyl)cyclopropyl]amino]5 (propylsulphonyl)-3H-1,2,3-triazolo[4,5-d]pyrimidin-3-yl)-5-(2-hydroxyethoxy)-cyclopentane-1,2-diol; (1 S-cis) 2-[[4-[7-Chloro-5-[(3,3,3-trifluoropropyl)thio]-3H-1,2,3-triazolo[4,5-d]-pyrimidin-3-yl]-2-cyclopenten-1-yl]oxy]-acetic acid, ethyl ester; [1S-(cis)]2-[[4-[7-Amino-5-[(3,3,3-trifluoropropyl)thio]-3H-1,2,3-triazolo[4,5-d]pyrimidin-3-yl]-2-cyclopenten-1-yl]oxy]-acetic acid, ethyl ester; [1 S-(cis)] 2-[[4-[7-Amino-5-[(3,3,3-trifluoropropyl)thio]-3H-1,2,3-triazolo[4,5-d]pyrimidin-3-yl]-2-cyclopenten-1-yl]oxy]-1-ethanol; [3aR-(3aα,4α,6α,6aα)]-2-[6-[7-Amino-5-[(3,3,3-trifluoropropyl)thio]-3H-1,2,3-triazolo[4,5-d]-pyrimidin-3-yl]-tetrahydro-2,2-dimethyl-4H-cyclopenta-1,3-dioxol-4-yloxy]ethanol; [3aR-(3aα,4α,6α,6aα)]-2-[6-[7-Bromo-5-[(3,3,3-trifluoropropyl)thio]-3H-1,2,3-triazolo[4,5-d]-pyrimidin-3-yl]-tetrahydro-2,2-dimethyl-4H-cyclopenta-1,3-dioxol-4-yloxy]ethanol; [3aR-[3aα,4α,6α(1R*,2S*),6aα]-2-[6-(7-Phenylcyclopropyl)amino]-5-[(3,3,3-trifluoropropyl)thio]-3H-1,2,3-triazolo[4,5-d]pyrimidin-3-yl]-tetrahydro-2,2-dimethyl-4H-1,3-dioxol-4-yloxy]ethanol; [3aR-[3aα,4α,6α(1R*,2S*),6aα]-6-[[7-[(3,4-Difluorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxol-4-ol; [3aR-[3aα,4α,6α(1R*,2S*),6aα]]-6-[[7-[(3,4-Difluorophenyl)cyclopropyl]amino]-5-(propylsulfonyl)-3H-1,2,3-triazolo[4,5-d]pyrimidin-3-yl]-tetrahydro-2,2-dimethyl-4H-cyclopenta-1,3-dioxol-4-ol; [3aR-[3aα,4α,6α(1R*,2S*),6aα]]-6-[5-(Butylthio)-7-[[2-(3,4-difluorophenyl)cyclopropyl]amino]-3H-1,2,3-triazolo[4,5-d]pyrimidin-3-yl]-tetrahydro-2,2-dimethyl-4H-cyclopenta-1,3-dioxol-4-ol; [3aR-[3aα,4α,6α(1 R*,2S*),6aα]]-2-[6-[[5-(Butylthio)-7-chloro-3H-1,2,3-triazolo[4,5-d]pyrimidin-3-yl]-tetrahydro-2,2-dimethyl-4H-cyclopenta-1,3-dioxol-4-yl]oxy]-ethanol; [3aR-[3aα,4α,6αα(1R*,2S*),6aα]]-2-[6-[[5-(Butylthio)-7-[2-phenylcyclopropyl]amino-3H-1,2,3-triazolo[4,5-d]pyrimidin-3-yl]-tetrahydro-2,2-dimethyl-4H-cyclopenta-1,3-dioxol-4-yl]oxy]-ethanol.

Methods of making ticagrelor and derivatives of ticagrelor can be found in U.S. Pat. Nos. 6,525,060 and 6,251,910, both of which are incorporated herein by reference for their teaching of methods of making ticagrelor and derivatives of ticagrelor.

Derivatives of ticagrelor of particular interest are those that decrease or lower AVP production by the hypothalamus but lacks anti-platelet effect with no or very little effect on coagulation. Also, of interest are derivatives of ticagrelor that decrease or lower hypothalamic AVP production but is not a P2Y12 receptor antagonist. Decreasing or lowering hypothalamic AVP production may occur at the level of AVP gene expression and processing of preproprotein to produce mature vasopressin (AVP) protein and may include secretion of AVP.

The disclosed compositions can be used in any of the disclosed methods.

The disclosed compositions can be pharmaceutical compositions comprising ticagrelor. That is, a pharmaceutical composition can be provided comprising a therapeutically effective amount of ticagrelor and a pharmaceutically acceptable carrier.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In the methods described herein, administration or delivery of the therapeutics to a subject can be via a variety of mechanisms. For example, the therapeutic can be formulated as a pharmaceutical composition.

Pharmaceutical compositions can be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for treating ADPKD, the kit comprising a composition comprising ticagrelor and instructions for how to administer the composition to a subject for treatment of ADPKD.

Also disclosed are kits for treating ADPKD, the kit comprising a composition comprising derivatives of ticagrelor and instructions for how to administer the composition to a subject for treatment of ADPKD.

EXAMPLES

Example 1

Materials and Methods:

The study evaluated the effect of increasing doses of ticagrelor from 0.05% to 0.25% (incremental doses of 0.05, 0.10, 0.15, 0.20 and 0.25%) administered to mice for 2 weeks and compared them with that obtained by administering increasing doses of clopidogrel bisulfate (20, 40 or 80 mg/kg bw/day). For this study adult B6D2 mice were used. Different doses of ticagrelor were administered embedded in diet. Clopidogrel bisulfate (Plavix® tablets) were powdered and dissolved in drinking water for administration. The concentration of clopidogrel in the water was adjusted on daily basis based on the water consumption by mice on the previous day.

Rodent diets containing ticagrelor at different concentrations were prepared as follows. 15 grams of ticagrelor was shipped to MP Biomedicals (Solon, Ohio, USA) for custom preparation of 10 kg of rodent chow in pellet form containing 0.15% ticagrelor. The custom-made diet was received and was stored at +4° C. Later in the study, for the preparation of diets containing 0.20% or 0.25%, the above custom-prepared diet (containing 0.15% ticagrelor) was used as a base and the required amount of ticagrelor was added. Diets containing 0.05 and 0.10% ticagrelor were prepared de novo.

Clopidogrel bisulfate was administered orally by mixing finely powdered Plavix® tablets (Bristol-Myers Squibb, New York, N.Y.) in drinking water. The concentration of the drug in the drinking water was adjusted daily based on the water consumption of the animals on the previous day. Three different doses (20, 40 and 80 mg/kg bw/day) were administered. Since it is not possible to work with more than 15 to 20 mice in metabolic cages at any given time, the experimental animals were handled in two batches in a staggered fashion. Urine samples were collected on day 0 (prior to the experimental period), on days 6/7 (end of the first week) and days 13/14 (end of the second week). Terminal blood samples were collected from the posterior vena cava at the time of euthanasia. Kidney tissues were collected and cortex and medulla were separated by sharp dissection and flash frozen for analysis. Within a few minutes after collection, blood samples were centrifuged at +4° C. and plasma was separated and frozen. Urinary AVP levels were assayed by ELISA. Table 1 shows the groups of mice used in the studies EDTA K-coated microtubes (Microvette®, Sarstedt, Nümbrecht, Germany). Plasma was separated by centrifugation within 30 min after collection and frozen at −80° C. The frozen samples were shipped in dry ice by FedEx to AstraZeneca (Mölndal, Sweden). At AstraZeneca R&D, the plasma concentration of ticagrelor was determined by liquid chromatography tandem mass spectrometry (LC-MS/MS). FIGS. 1-5 show the data obtained.

The data presented in FIGS. 1 through 5 clearly show that administration of ticagrelor induces a dose-related decrease in urinary concentrating ability in mice, as assessed by increase in urine output, associated with a corresponding decrease in urine osmolality. This decrease in urine concentrating ability is apparently due to a comparable dose-related decrease in urinary AVP excretion. Since AVP levels in 24-hour collection of urine are a reliable surrogate for the circulating plasma levels of AVP over the same period, it is logical to conclude that administration of ticagrelor results in dose-dependent decrease in AVP production by the hypothalamus. The modest alterations in urinary parameters in the control group over time (from day 0 to 14) are often observed apparently due to the stress associated with moving the mice from regular to metabolic cages and vice versa. Their magnitude is far less than the effect seen with the increasing doses of ticagrelor.

It was discovered that administration of ticagrelor (Brilinta®) to normal mice causes a dose-dependent decrease in urinary excretion of arginine vasopressin (AVP), a reliable surrogate for circulating levels of AVP. Circulating levels of AVP are critical for the cyst growth in ADPKD. So, the therapeutic potential of ticagrelor in slowing down the cyst growth in ADPKD is currently being evaluated. This approach can have minor side effects only as compared to the significant side effects with other therapies under development.

AVP or the anti-diuretic hormone, elaborated by hypothalamus in the brain, plays a critical role in body water homeostasis by regulating the urinary excretion of water. AVP, acting through its V2 receptor, is a major stimulus for production of cyclic AMP (cAMP) in the kidney collecting

TABLE 1

| Group ID | Controls | Tica-0.05 | Tica-0.10 | Tica-0.15 | Tica-0.20 | Tica-0.25 |
| --- | --- | --- | --- | --- | --- | --- |
| Ticagrelor Dose in Food (wt/wt) | N/A | 0.05% | 0.10% | 0.15% | 0.20% | 0.25% |
| Number of Mice (N) | 6 | 5 | 5 | 5 | 5 | 5 |

Discussion

Effect of Different Doses of Ticagrelor on Urinary AVP, Urine Output and Urine Osmolality in Mice:

Different doses of ticagrelor (0.05 to 0.25%) were administered to mice embedded in standard rodent chow (w/w) for 14 days. Twenty-four hour urine samples were collected from the mice by placing them in individual plastic metabolic cages (1 mouse/cage) for two consecutive days, with free access to food and water. Urine samples in the metabolic cages were collected under a layer of light mineral oil. The volumes of urine samples collected were recorded. Urine samples were centrifuged to remove particulate matter. Clear supernatants thus obtained were used for analysis. Blood samples were collected at the time of euthanasia on day 14, as per the protocol recommended by the AstraZeneca for samples destined for the determination of plasma ticagrelor. Briefly, under isoflourane anesthesia, blood from the posterior vena cava was collected and transferred to duct, the site of osmotic water reabsorption. However, collecting ducts are also the predominant site of the origin of cysts in the kidney. cAMP also promotes cyst growth.

Incidentally, the circulating levels of AVP are increased in human ADPKD and in all animal models of ADPKD, where it has been ascertained. This can be due to compensatory increase in the production of AVP by hypothalamus in response to reduced concentrating capacity of the polycystic kidneys. Thus, AVP-V2 receptor-cAMP axis plays a critical role in ADPKD progression. Whatever may be the causative factors for the increased AVP production, in pre-clinical studies in rodent models of ADPKD, vasopressin V2 receptor antagonists (OPC-31260 and tolvaptan) consistently inhibited cystogenesis by reducing cAMP production in the kidney. In subsequent clinical trials, the efficacy of tolvaptan for the treatment of ADPKD was established.

ATP/UTP-activated P2Y2 and ADP-activated P2Y12 receptors were identified as potential targets for the treatment of acquired nephrogenic diabetes insipidus (NDI) induced by lithium, a drug still widely used for the treatment of bipolar disorder. Bipolar disorder has a high prevalence among war Veterans, because post-traumatic stress disorder (PTSD) predisposes war Veterans to bipolar disorder. P2Y12 receptor is expressed in the kidney and hypothalamus, and clopidogrel bisulfate (Plavix®), an anti-clotting drug, which blocks platelet P2Y12 receptor, were found to significantly ameliorate lithium-induced NDI in rodent models. Ticagrelor is another P2Y12 receptor antagonist marketed as Brilinta®. Unlike clopidogrel, ticagrelor is not a pro-drug, and it reversibly binds to P2Y12 receptor, thus it has specific advantages over clopidogrel. It was determined that administration of ticagrelor to normal mice (B6D2 genetic background) causes a dose-dependent decrease in the production of AVP as assessed by AVP levels in 24-hour urine collections (a reliable surrogate for circulating levels of AVP over 24 hours), associated with a dose-dependent decrease in urinary concentrating ability as assessed by urine output and osmolality, thus establishing a reduced activity of AVP-V2 receptor-cAMP axis in ticagrelor-treated mice (FIGS. 2-5). The ticagrelor-induced reduction in AVP-V2 receptor-cAMP can decrease cyst growth in ADPKD.

It should be noted that the effects shown in FIGS. 2-5 are unique to ticagrelor, and could not be seen with either clopidogrel or with prasugrel (Effient®) another P2Y12 receptor antagonist. Although ticagrelor does not pass through the blood brain barrier (BBB), and thus has limited exposure to brain, yet it can act on hypothalamus. It is because the hypothalamus or the posterior pituitary gland lacks a BBB, and thus is easily accessible to circulating drugs and agents. Hence, ticagrelor can have a direct effect on hypothalamus, and thus reduce AVP production. This effect of ticagrelor can also not be mediated through P2Y12 receptor, because blockade of P2Y12 receptor in primary cultures of rat hypothalamic cells by PSB-0739, a potent and selective antagonist, actually increased the expression of AVP. Reducing AVP production in a controlled fashion (by adjusting the dose of ticagrelor) can have specific advantages over blockade of V2 receptor by the use of selective receptor blockers for the treatment of ADPKD.

Figure 4:
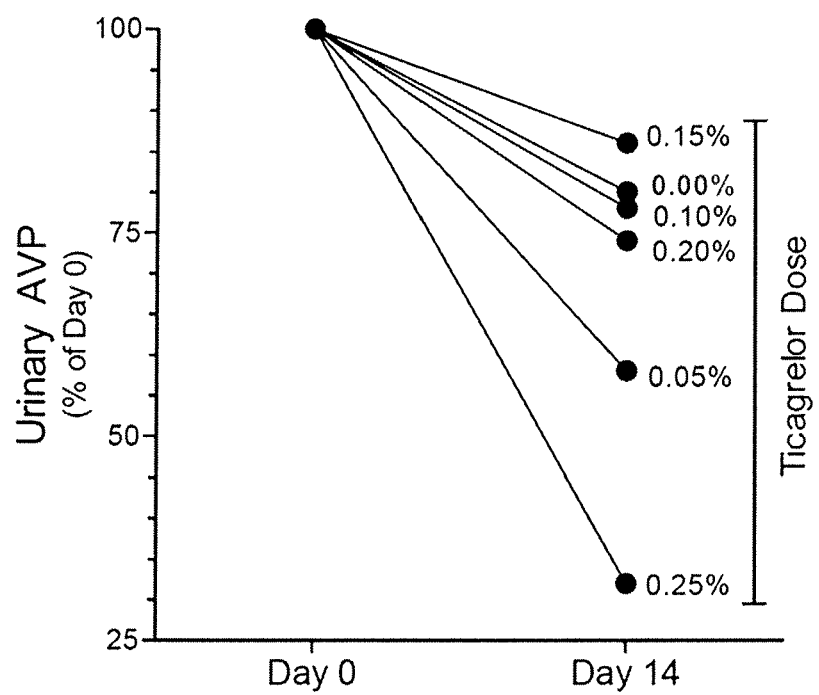
FIG. 4 is a graph showing the changes in the mean urine AVP excretion in groups of mice fed different concentrations of ticagrelor in the food as a function of time. The lines show the percent fall in urine AVP within each group from day 0 to day 14 (i.e., day 0 vs. day 14 in the same group).
Figure 5A:
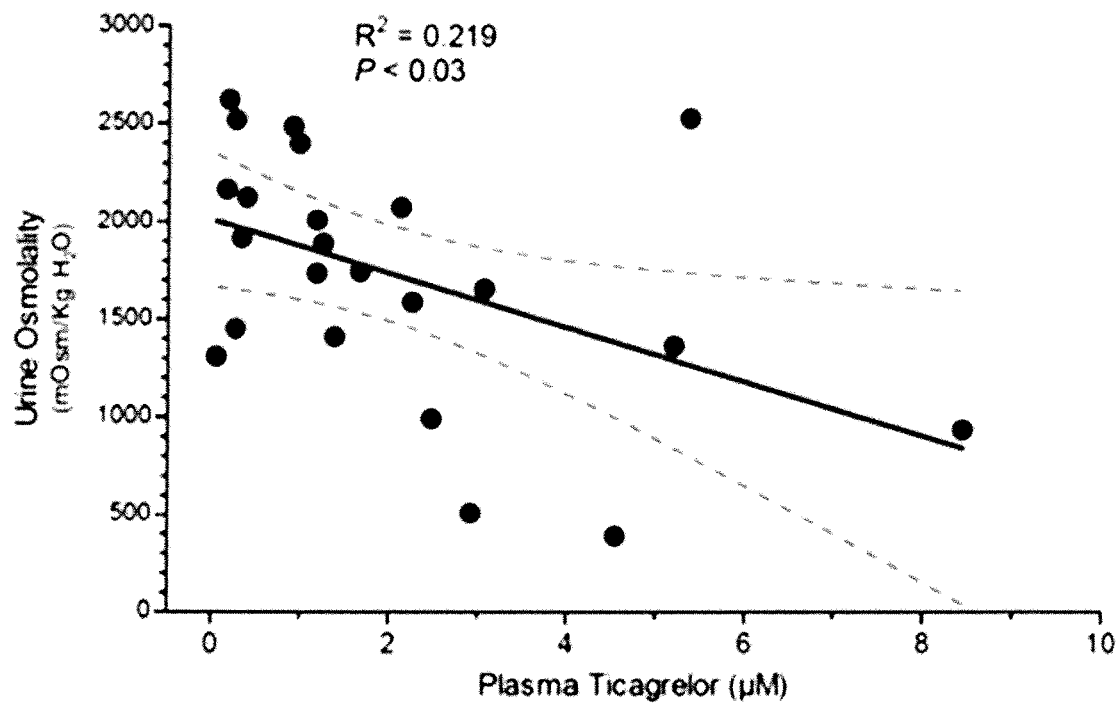
FIGS. 5A and 5B are regression analysis graphs. A: Regression analysis showing significant relationship between plasma ticagrelor and urine osmolality in the mice. B: Regression analysis showing significant relationship between plasma ticagrelor and urinary AVP excretion in the mice.
Figure 5B:
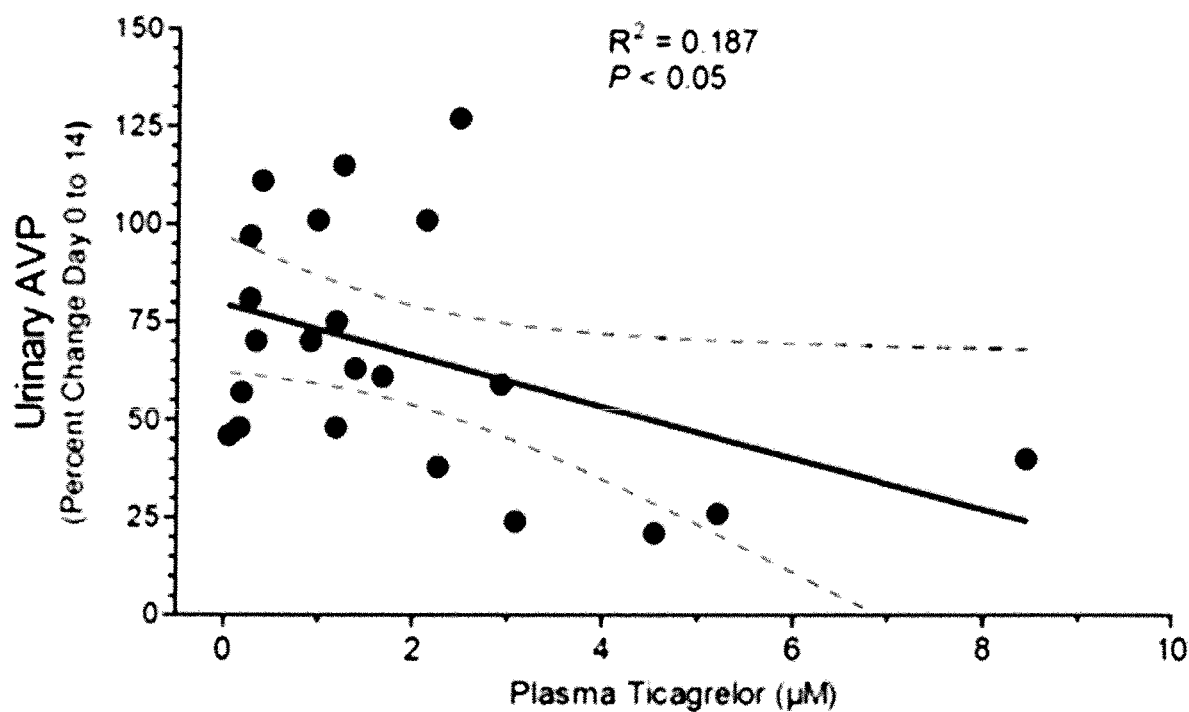

FIG. 4 confirms that significant reduction in urine concentrating ability induced by 0.25% ticagrelor in the food was associated with a marked decrease in urinary AVP (vasopressin), a surrogate for the circulating AVP levels. Furthermore, these data also reveal that lower doses of ticagrelor have minimal effect on urinary AVP. Note: The modest fall in urinary AVP in the control group over time (from day 0 to 14) is often observed apparently due to the stress associated with moving the mice from regular to metabolic cages and vice versa.

Further processing of data using regression analysis revealed a significant relationship between plasma ticagrelor and urine osmolality (FIG. 5A) or urinary excretion of AVP (FIG. 5B) in the mice fed different concentrations of ticagrelor in the food. Similar to the data shown in FIGS. 3 and 4 for urine osmolality and AVP, respectively, the relation was more pronounced at plasma ticagrelor levels above 1.30 µM, corresponding to a dose of 0.15% or above. These data further confirm that higher plasma concentrations of ticagrelor definitely result in decreased urine concentrating ability associated with lower AVP levels, whereas at lower concentrations of ticagrelor the effect is variable or has less impact.

As, these data suggest that the observed dose-dependent decrease in urinary AVP is due to the administration of ticagrelor, which in turn is translated to a dose-dependent decrease in urinary concentrating ability as assessed by urine osmolality, the latter cannot be achieved without the decreased activity of AVP-V2 receptor-cAMP axis in the renal collecting duct cells as a function of plasma levels of ticagrelor. In other words, ticagrelor has the potential to decrease cAMP production in the renal collecting duct cells in a dose-dependent manner, which is the desired effect for a candidate molecule to be developed as a drug for the treatment of ADPKD.

Example 2

Primary cultures of rat inner medullary collecting duct (IMCD) cells were prepared. When the cells became 70-80% confluent, the medium was changed to relative starvation mode (low FBS), and used for testing the effect of Desmopressin (dDAVP), a V2 receptor-selective analogue of AVP, and/or ticagrelor. Cells were incubated for 48 h with ticagrelor ranging from 1.5 to 25 µM. During the second 24 hours, cells were challenged with dDAVP (20 nM). At the end of the incubation period, cells were harvested, RNA extracted, reverse transcribed and subjected to real-time PCR to determine the expression of AQP2 and AQP3 genes relative to the expression of the housekeeping genes (β-actin or GAPDH).

Figure 6A:
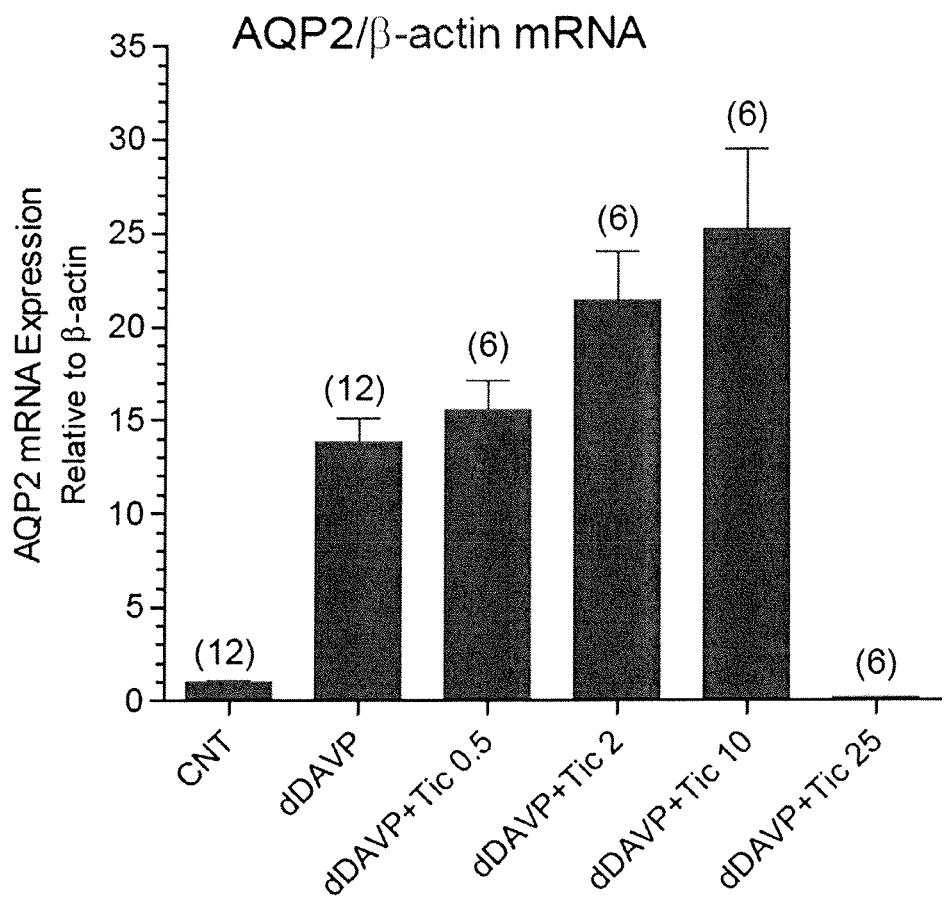
FIGS. 6A-C show the effect of ticagrelor on the mRNA expression of AQP2 (A) and AQP3 (B) relative to the expression R3-actin and the effect of ticagrelor on the mRNA expression of AQP2 relative to GAPDH (C) in primary cultures of rat inner medullary collecting duct (IMCD) cells. Cells were incubated with different concentrations of ticagrelor (0.5 to 25 µM) for 48 hours. During the second 24 hours, the cells were challenged with dDAVP (20 nM). The numbers in parentheses above the bars indicate the number of culture wells. Statistical values are shown in the tables.
Figure 6B:
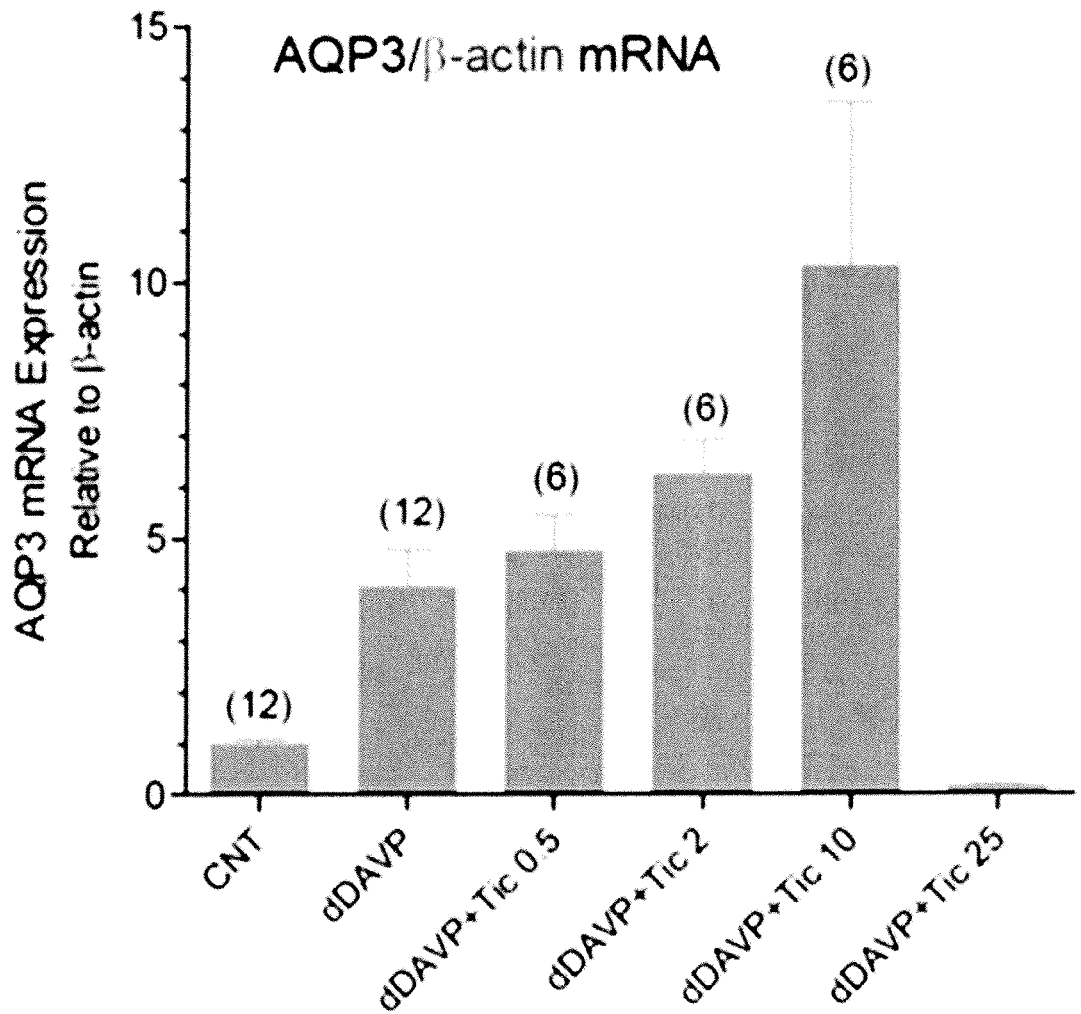
Figure 6C:
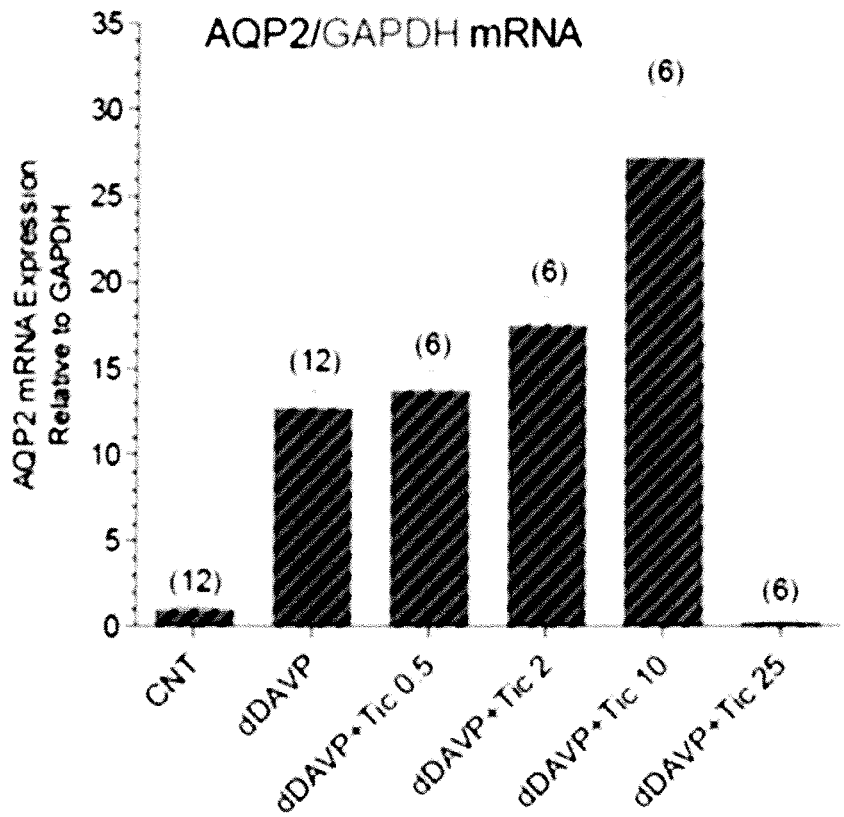

Results (FIGS. 6A-C) are presented as percent of the values in control incubations without any addition of agents. FIGS. 6A-C show the effect of different concentrations of ticagrelor on dDAVP (20 nM)-induced AQP2 or AQP3 expression relative to p-actin expression in primary cultures of rat IMCD cells. Two independent assays on primary cultures of IMCD cells derived from two different rats at different times were used, and the data obtained were pooled for analysis and presentation in the graphs. Data were analyzed by analysis of variance (ANOVA) followed by Tukey-Kramer Multiple Comparison Test. The numbers in parentheses above the bars indicate the number of culture wells. Ticagrelor showed a tendency for concentration-dependent enhancement of the effect of dDAVP on AQP2 and AQP3 mRNA expression. The enhancements at 2 or 10 µM are statistically significant (ANOVA followed by Tukey-Kramer Multiple Comparison Test)

Figure 7:
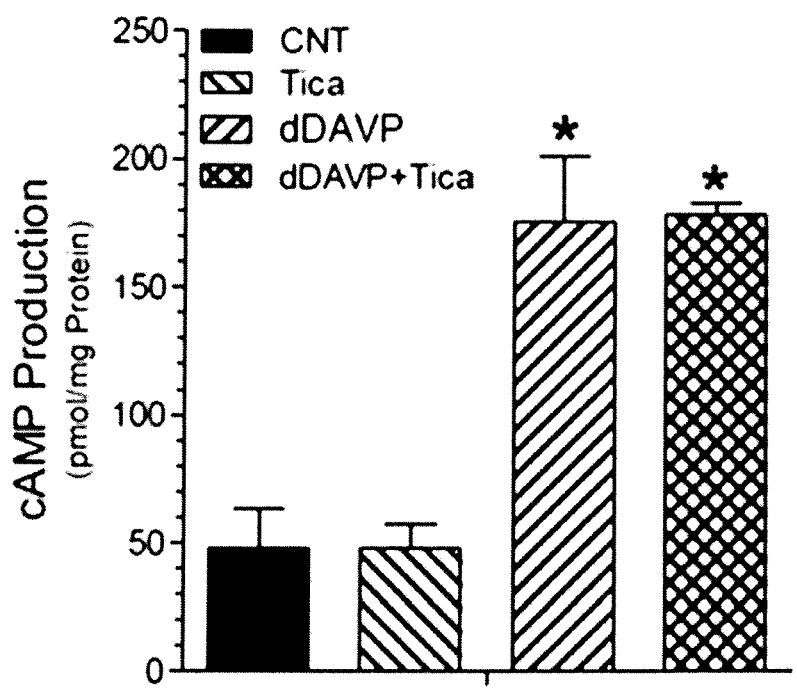
FIG. 7 is a graph showing the effect of ticagrelor on dDAVP-induced cAMP production in primary cultures of rat IMCD cells: Cells were incubated for 48 h with ticagrelor (5 µM). During the second 24 hours, cells were challenged with dDAVP (20 nM). N=3 Transwell® inserts for condition. *significantly different (P<0.01) when compared to CNT or Tica groups.

Blockade of P2Y12 receptor in IMCD cells by ticagrelor augmented the dDAVP-induced expression of both AQP2 and AQP3 genes. The augmentative effect was seen even at ticagrelor concentration of 2 µM, and is more prominent at 10 µM. These findings are similar to the ones the investigators observed previously by the use of PSB-0739, a potent, selective and reversible antagonist of P2Y12 receptor. Thus, it appears that as expected, these effects of ticagrelor on IMCD cells are mediated through P2Y12 receptor. However, at higher concentrations (25 µM), ticagrelor has a negative effect, suppressing the gene expression to a very low level. It should be noted that in general, for drugs that are freely filtered at the glomeruli, and are not secreted by the tubules, the concentrations in the distal nephron or collecting duct in vivo are at least 10-fold higher than their plasma concentrations. So, 10 µM of ticagrelor used here in the culture dish is equivalent to 1 µM of ticagrelor in the plasma in vivo.

dDAVP acting through the vasopressin V2 receptor in IMCD cells stimulates the production of cAMP (FIG. 7). In the collecting ducts in vivo, in the short-term AVP increases cellular cAMP levels to cause translocation of AQP2 protein from the subapical vesicles to apical plasma membrane, and thus increase the water permeability of the apical plasma membrane, the rate limiting barrier for transepithelial water transport. In the long-term, increased cellular cAMP levels induce transcriptional activation of AQP2 and other genes. Hence, the investigators evaluated the effect of ticagrelor on desmopressin-induced cAMP production in primary cultures of rat IMCD cells. Primary cultures of rat IMCD cells were prepared and incubated with desmopressin with/without ticagrelor (5 μM) as described above. For cAMP assay, the medium was gently aspirated, 200 μl of 0.1 M HCl was added to each insert and incubated for 20 min at room temperature. Then cells were scrapped off the semi-permeable support and lysed by pipetting up and down. The cell lysate was centrifuged at 1,000×g for 10 min. cAMP concentration in the supernatant was determined by an EIA kit (Cayman Chemical Co.) and normalized to the protein content of the wells (Pierce™ BCA Protein Assay Kit, Rockford, Ill.).

Stimulation of IMCD cells with 20 nM of desmopressin caused 3.6-fold increase in cellular cAMP levels. Addition of 5 μM ticagrelor did not have any significant effect on desmopressin-induced cAMP levels. This finding indicates that at the concentration used, ticagrelor does not interfere with the action of desmopressin on the cAMP production in the collecting duct. A higher concentration of ticagrelor (10 μM) can have an effect on the desmopressin-stimulated cAMP production in the IMCD. However, it should be noted that even at 2 μM concentration, ticagrelor showed a tendency to augment the effect of dDAVP on AQP2 and AQP3 expression. Furthermore, the concentration of ticagrelor used here (5 μM) in cell cultures, when translated into in vivo conditions in an intact animal correspond to about 0.5 μM ticagrelor in blood plasma. Based on this, it appears that the observed in vivo effect of ticagrelor at low plasma concentrations on urinary osmolality is predominantly due to low AVP levels, but not on the IMCD. It is because, in isolated IMCD cells, ticagrelor at a concentration of 5 μM did not suppress dDAVP-induced increases in cAMP production or APQ2/AQP3 expression.

Example 3

Figures 8A, 8B:
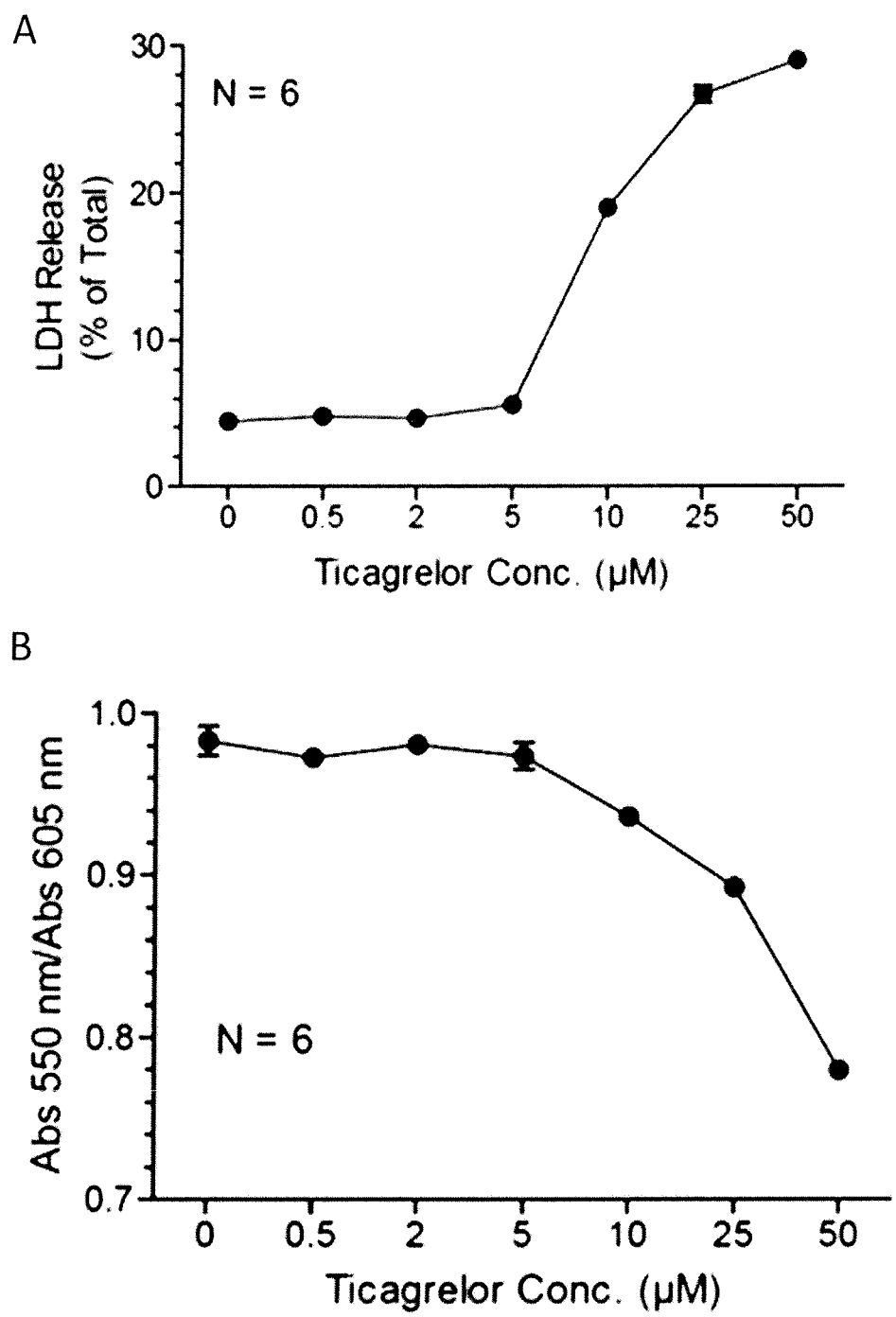
FIGS. 8A and 8B are graphs showing the results of cytotoxicity assays. A: LDH Cytotoxicity Assay: Effect on different concentrations of ticagrelor on the release of LDH by primary cultures of rat IMCD cells into the culture medium. Higher LDH release indicates increased cytotoxicity. Results are mean±SE of 6 wells for each concentration of ticagrelor. B: Cell Cytotoxicity Assay: Effect on different concentrations of ticagrelor on cell cytotoxicity. Higher ratio of A550/A605 indicates more viable cells in the well. Results are mean±SE of 6 wells for each concentration of ticagrelor.

Based on the above observations in IMCD cells, where different concentrations of ticagrelor were used, it appears that at higher concentrations, ticagrelor can have an effect on the IMCD cells in general. At a concentration of 25 μM, ticagrelor almost completely suppressed the gene expression of AQP2 and AQP3. So, the effect of ticagrelor on cell viability was investigated using two approaches as follows (FIGS. 8A and 8B).

LDH Cytotoxicity Assay: Lactate dehydrogenase (LDH) is a cytosolic enzyme released into the cell culture medium when the plasma membrane is damaged. So, quantification of extracellular LDH activity in the medium indicates the viability of the cells exposed to agents. Thermo Scientific™ Pierce™ LDH Cytotoxicity Assay Kit was used, which is a simple and reliable colorimetric method for quantifying cellular toxicity. The kit is based on a coupled enzymatic reaction in which LDH catalyzes the conversion of lactate to pyruvate via NAD+ reduction to NADH. Diaphorase then uses NADH to reduce a tetrazolium salt to red formazan product that can be measured at 490 nm. The level of formazan formation is directly proportional to the amount of LDH released into the medium, which is indicative of cytotoxicity. Primary cultures of rat IMCD cells grown in collagen coated 96-well plate were incubated with different concentrations of ticagrelor for 24 hours. LDH released into the medium was assayed using the kit as per the manufacturer's instructions. Total LDH activity was determined by adding lysis buffer to the designated wells. Absorbance readings of the test wells were converted into the percent values in relation to the maximum LDH activity. Results are presented in FIG. 8A.

Cell Cytotoxicity Assay: Toxicity of ticagrelor toward IMCD cells was colorimetrically assayed using Cell Cytotoxicity Assay Kit from Abcam. This kit uses a proprietary water-soluble dye that changes its absorption spectra upon cellular reduction. The absorption ratio change is directly proportional to the number of living cells on the plate.

According to the manufacturer, this assay has higher sensitivity compared to the tetrazolium based colorimetric assays (such as MTT). Primary cultures of rat IMCD cells grown in collagen coated 96-well plate were incubated with different concentrations of ticagrelor for 24 hours. Cell cytotoxicity was assayed as per the manufacturer's instructions. Absorbance changes at 570 nm and 605 nm were monitored. The ratio of A570 and A605 were used to determine the cell viability in each cell. Results are presented in FIG. 8B.

As compared to the currently available alternative for reduction in the activity of AVP and production of cAMP in the kidney, i.e., vasopressin V2 receptor antagonism by tolvaptan, the disclosed invention has specific and clear advantages. First, administration of tolvaptan blocks the vasopressin V2 receptor and thus causes severe polyuria (loss of water in the urine), nocturia (frequent urination in the night), thirst and dry mouth in a vast majority of the patients. Other common side effects of tolvaptan are constipation, loss of appetite, dry skin, nausea, vomiting, and potential for acute liver failure. Furthermore, tolvaptan is metabolized by the CYP3A4 system, which may result in increased interactions with other medications. Although tolvaptan exhibits dose-related pharmacokinetics, it is unpredictable in ADPKD patients (or animals) who have varying degrees of renal dysfunction, thus necessitating therapeutic drug monitoring. In view of this, the long-term use of tolvaptan for the treatment of ADPKD is not feasible in many patients. It should be noted that tolvaptan was originally developed for the treatment of hyponatremia, which represents a shorter period of treatment. In contrast, the only major side effect of long-term administration of ticagrelor is uncontrolled bleeding from wound or internal ulcers. Other side effects reported are minor, and tolerable.

Besides, unlike tolvaptan, ticagrelor has been developed and evaluated for long-term use in patients with cardiovascular risk factors (e.g., heart attack or stroke). Second, the ability of ticagrelor to reduce the production of AVP by the hypothalamus is an off-target effect, and is not related to its original intended use to block P2Y12 receptor antagonist to function as a blood thinner. It should be noted that the inventors observed that clopidogrel bisulfate (Plavix®), another selective P2Y 2 receptor blocker and blood thinner, did not have such an effect on the production of AVP by the hypothalamus. In fact, they showed that direct inhibition of P2Y12 receptor in cultured cells by PSB-0739, a potent, selective and reversible antagonist, actually increased the expression of AVP. At present the molecular mechanisms of the observed inhibitory effect of ticagrelor on the hypothalamus are not known, thus making it difficult to mimic its action on the hypothalamus by other drug manufacturers. It takes considerable research to unravel the molecular mechanisms by which ticagrelor inhibits the production of AVP in the hypothalamus. In contrast, tolvaptan does not possess such tacit mechanism of action, and its therapeutic effect both in hyponatremia and ADPKD is mediated through the same known mechanism, i.e., blockade of vasopressin V2 receptor, thus making it vulnerable to competition. Finally, it has been shown that chronic blockade of vasopressin V2 receptor by tolvaptan results increased endogenous production of AVP. Since, AVP has two other receptors, namely, V1a (in blood vessels) and V1b (in liver), the effects of chronically increased AVP levels through these two receptors is not known. In contrast, administration of ticagrelor decreases AVP levels in a controllable manner, and so the V1a and V1b receptors are not overstimulated.

Discussion

The results obtained in these experiments have significant short- and long-term impact on the treatment or management of ADPKD, the most common form of PKD. In the short-term, the results offer a viable treatment strategy for ADPKD with fewer or tolerable side effects. Ticagrelor (Brilinta®) has been in clinical use for about 5 years in the United States so ticagrelor can be directly tested in ADPKD patients for its therapeutic potential. Currently V2 receptor blockers, such as tolvaptan, have been shown to slow down the cyst growth in experimental models of ADPKD, and are undergoing clinical trials. The major side effect of long-term use of ticagrelor is uncontrolled bleeding from wounds or internal ulcers. Other side effects reported for ticagrelor are minor and tolerable. Second, it has been shown that chronic blockade of vasopressin V2 receptor by tolvaptan results in increased endogenous production of AVP. Since AVP interacts with two other receptors, namely V1a (in blood vessels) and V1b (in liver), the effects of chronically increased AVP levels through these two V1 receptor subtypes is not known. In contrast, administration of ticagrelor decreases AVP levels in a dose-dependent fashion, and so the V1a and V1b receptors are not overstimulated. Finally, in order to reduce renal cAMP levels, tolvaptan has to swim against two opposing forces, namely increased levels of AVP and expression of V2 receptor in ADPKD. In contrast, by its potential to reduce circulating levels of AVP, ticagrelor essentially eliminates one current, and thus reduces the availability of the ligand for the increased V2 receptor expression in ADPKD.

Example 4

This study is proposed to evaluate the efficacy of ticagrelor administration in slowing down the growth of renal cysts in rodent models of ADPKD.

This study can also compare the efficacy of ticagrelor with tolvaptan in slowing down cyst growth, and on the major side effect, the polyuria. It is expected that (i) administration of ticagrelor slows down renal cyst growth, and (ii) the slowing down process is associated with minimal and tolerable loss of water in urine (polyuria) as compared to the use of tolvaptan. Thus, a new therapy for ADPKD can be developed using a readily available drug (ticagrelor), which has a proven safety record and is well tolerated by patients on a chronic treatment regimen. In addition, administration of ticagrelor has the added benefit of prevention of acute cardiovascular and cerebrovascular events (heart failure and stroke) in high risk patients with ADPKD, a benefit not offered by the use of V2 receptor blocks, such as tolvaptan.

The study design consists of evaluating the effect of administration of ticagrelor in mouse models of ADPKD. Syngeneic mice without ADPKD can serve as controls. One proposed ADPKD model uses mice lacking Pkd1 gene, which accounts for 85% of the human ADPKD patients. The other ADPKD model uses mutant mice lacking Pkd2 gene, which is responsible for 15% of prevalence of ADPKD in humans. Since germ line and/or whole body deletion of Pkd1 or Pkd2 can be lethal or the mice may or may not survive for long time due to rapidly progressing disease, inducible and renal collecting duct specific knockout of Pkd1 or Pkd2 genes can be used. Cryopreserved embryos of Pkd1 or Pkd2 floxed mice are available from the Jackson Laboratory, which rederives the mutant mouse lines and supplies the breeders. The Jackson Laboratory also provides a variety of Cre-ER mice with different promoters and Nestin-CRE mice. For example, by crossing Pkd1-floxed mice or Pkd2-floxed mice with Nestin-CRE mice, "mosaic" model of ADPKD may be obtained. The "mosaic" ADPKD mouse model is a slowly progressing PKD model, similar to the one seen in human patients, and thus allows us to test the effect of drugs. The effectiveness of ticagrelor as a therapeutic, used singularly or in combination with other drugs, for treating ADPKD and managing its symptoms may be determined. In addition, the effectiveness of ticagrelor in comparison to vasopressin V2 receptor antagonists, such as tolvaptan, on the progression of ADPKD may be evaluated in these mutant mice.

i. To Establish Optimum Doses for Ticagrelor and Tolvaptan vis-à-vis AVP-V2 Receptor-cAMP Axis.

The optimum dose of ticagrelor and tolvaptan can be determined to achieve a comparable level of activity of AVP-V2 receptor-cAMP axis, the key determinant of cyst growth. A published report administered tolvaptan concentrations between 0.01% and 0.30% in food in DBA/2FG-pcy mouse model of ADPKD, and reported the optimum concentration as 0.10%. However, it is possible that each model of ADPKD may have its own sensitivity toward tolvaptan. Similarly, as shown in FIGS. 1-4 and 5, ticagrelor concentrations between 0.05% and 0.25% in food were evaluated on the urinary AVP excretion and concentration in normal mice, and a wide range of effects were found. In view of the observed variations, dose-effects for both drugs can be evaluated by administering different concentrations in food and determining the level of activity of AVP-V2 receptor-cAMP axis as follows. The "mosaic" ADPKD mouse model, described above, can be administered different concentrations of ticagrelor and tolvaptan in the food to control or wild type WT mice and mosaic Pkd 1 or mosaic Pkd 2 knockout mice. Table 2 gives the doses of ticagrelor and tolvaptan to be tested and the number of mice used for each dose.

TABLE 2

Proposed Doses and number of mice for each dose.

| | Ticagrelor Doses | | | | | Tolvaptan Doses | | | | |
|---|---|---|---|---|---|---|---|---|---|---|
| | 0 | 0.10% | 0.15% | 0.20% | 0.25% | 0 | 0.03% | 0.10% | 0.20% | 0.30% |
| WT | N = 5 | N = 5 | N = 5 | N = 5 | N = 5 | N = 5 | N = 5 | N = 5 | N = 5 | N = 5 |
| Pkd 1 knockout | N = 5 | N = 5 | N = 5 | N = 5 | N = 5 | N = 5 | N = 5 | N = 5 | N = 5 | N = 5 |
| Pkd 2 knockout | N = 5 | N = 5 | N = 5 | N = 5 | N = 5 | N = 5 | N = 5 | N = 5 | N = 5 | N = 5 |

The drugs will be administered mixed in the food. Treatment starts at 2 to 3 months age and lasts for one month, at which point mice are humanely euthanized. Blood and kidney samples can be collected for analysis. Twenty-four hour urine samples can be collected prior to, at the mid-point and towards the end of the treatment period. Urine can be analyzed for output, osmolality and AVP content. Plasma samples can be analyzed for ticagrelor. Kidney samples can be analyzed for the expression of V2 receptor mRNA and cAMP levels, and AQP2 mRNA and protein. The morphological structure of the collecting duct can be examined for cyst development. Based on the data collected the doses of ticagrelor and tolvaptan that result in comparable levels of decrease in cAMP levels in the kidney, and comparable levels of polyuria can be determined. However, from the point of therapeutic effect in ADPKD, comparable decreases in cAMP levels are more relevant than comparable degree of decreases in polyuria. The data collected can also provide information on the level of AVP decrease in ticagrelor vs. increase in tolvaptan-treated mice at the optimum doses selected. The optimum doses of the two drugs that established can be used in the following experiments in Pkd1 and Pkd2 mosaic models of ADPKD.

ii. Comparative Effect of Ticagrelor and Tolvaptan on the Progression of Cyst Growth in Pkd1 or Pkd2 Mosaic Models of ADPKD.

After establishing optimum doses for ticagrelor and tolvaptan, groups of mosaic Pkd 1 or Pkd 2 knockout mice and their WT (Pkd 1 floxed or Pkd 2 floxed) mice can be subjected to treatment as shown in table 3. Cohorts of mosaic mutant mice and WT floxed mice do not receive any treatment (N=10 mice/group). Treatment with the drugs will start when the mice are 2- to 3-month old and will continue until the time of euthanasia (approx. 6 to 7th month postnatal). Twenty-four hour urine samples will be collected prior to the treatment, once in every month during the treatment period and then towards the end of treatment.

TABLE 3

Proposed Doses and number of mice per treatment group

|  | Ticagrelor | | Tolvaptan | |
| --- | --- | --- | --- | --- |
|  | 0 | OPD* | 0 | OPD* |
| Pkd 1 floxed | N = 10 | N = 10 | N = 10 | N = 10 |
| Pkd 1 knockout | N = 10 | N = 10 | N = 10 | N = 10 |
| Pkd 2 floxed | N = 10 | N = 10 | N = 10 | N = 10 |
| Pkd 2 knockout | N = 10 | N = 10 | N = 10 | N = 10 |

*Optimum Dose Established in earlier study

Blood and kidney samples can be collected at the time of euthanasia. Using standard parameters, the severity of structural and functional aspects of ADPKD can be assessed in the treated and untreated mice and the controls. The structural parameters are: i) body weight, ii) kidney weight, iii) kidney/body weight ratio, iv) number of cysts per unit area of the kidney under microscope, v) average size of the cysts in the kidney under the microscope, vi) cell proliferation in the kidney, and vii) apoptosis in the kidney. The functional parameters to be assessed are: i) urine output and osmolality, ii) urine AVP levels, iii) plasma chemistry, including blood urea nitrogen (BUN); v) eGFR (estimated glomerular filtration rate), vii) analysis of kidney samples for the expression of V2 receptor mRNA and cAMP levels, and AQP2 mRNA and protein. The data collected thus can reveal the effects of ticagrelor or tolvaptan in Pkd 1 and Pkd2 models of ADPKD when administered at their respective doses on: 1) severity of polyuria and associated urine and kidney parameters; ii) progression of ADPKD as assessed by number and size of the cysts in the kidney; and iii) renal functional impairment, if any, as assessed by BUN and eGFR determinations. Thus, this study evaluates the therapeutic potential of ticagrelor in ADPKD, as well as its side effects in comparison with that of tolvaptan.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

What is claimed is:

1. A method for lowering circulating levels of AVP in a subject, the method comprising administering to the subject an effective amount of a composition comprising an effective amount of ticagrelor, thereby lowering circulating levels of AVP in the subject.

2. The method of claim 1, wherein the subject has a disease, wherein the disease is selected from the group consisting of hypertension, preeclampsia, congestive heart failure, cardiorenal syndrome, cirrhosis of liver, diabetic ketoacidosis, post-traumatic stress disorder (PTSD), countering effect of loop diuretics, high altitude pulmonary edema, autism, syndrome of inappropriate antidiuretic hormone (SIADH), autosomal dominant polycystic kidney disease (ADPKD), dilutional hyponatremia and disease associated with elevated activity of AVP-V2 receptor-cAMP axis.

3. The method of claim 1, wherein lowering circulating level of AVP reduces signaling by AVP-dependent V2 receptor in a cell of the subject.

4. The method of claim 1, wherein lowering circulating level of AVP reduces signaling by AVP-dependent V1 receptor in a cell of the subject.

5. The method of claim 3, wherein reduced signaling by AVP-dependent V1 or V2 receptor slows or reverses a disease associated with elevated AVP in the subject.

6. The method of claim 3, wherein the cell is a renal collecting duct cell.

7. The method of claim 6, wherein the renal collecting duct cell is or comprises a principal cell.

8. The method of claim 7, wherein the principal cell has a lower cAMP level.

9. The method of claim 8, wherein lowering of cAMP level results in a decrease number of aquaporin proteins on apical surface of the principal cell.

10. The method of claim 9, wherein lowering of cAMP level results in a decreased expression of aquaporin genes.

11. The method of claim 9, wherein the aquaporin proteins are selected from the group consisting of aquaporin protein 2 (AQP2) and aquaporin protein 3 (AQP3).

12. The method of claim 9, wherein the aquaporin protein is aquaporin protein 2 (AQP2).

13. The method of claim 9, wherein the decreased number of aquaporin proteins on apical surface of the principal cell result in a decreased re-absorption of water by the principal cell or renal collecting duct cell, increased urine output, decreased urine osmolality, and/or decreased urinary AVP excretion.

14. The method of claim 13, wherein decreased urinary AVP excretion positively correlates with a decreased plasma AVP level.

15. The method of claim 1, wherein the subject is a human, non-human primate, rabbit, sheep, rat, dog, cat, pig, or mouse.

16. The method of claim 1, wherein the subject has been diagnosed with a need for treatment of ADPKD prior to the administering step.

17. The method of claim 1, wherein the subject is in need of treatment of a kidney disease.

18. The method of claim 1, further comprising administering one or more additional therapeutic.

19. The method of claim 1, wherein the composition comprising ticagrelor is administered orally, intravenously, subcutaneously or intramuscularly, as an implant or patch, or via a needle or microneedles.

20. The method of claim 1, wherein the step of administering to the subject a composition comprising an effective amount of ticagrelor is a long-term treatment regimen, wherein the long-term treatment regimen is at least 2 weeks.

* * * * *